(12) United States Patent
Giesing et al.

(10) Patent No.: US 7,056,660 B1
(45) Date of Patent: *Jun. 6, 2006

(54) METHOD FOR CHARACTERIZING DISSEMINATED AND MICROMETASTASIZED CANCER CELLS

(75) Inventors: Michael Giesing, Recklinghausen (DE); Frank Austrup, Recklinghausen (DE); Gerhard Driesel, Recklinghausen (DE); Claudine Eder, Recklinghausen (DE); Nico Feifel, Recklinghausen (DE); Beatrix Holewa, Recklinghausen (DE); Bernhard Suchy, Recklinghausen (DE); Peter Uciechowski, Recklinghausen (DE)

(73) Assignee: Michael Giesing, Lienen (DE)

(*) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/485,879

(22) PCT Filed: Aug. 24, 1998

(86) PCT No.: PCT/EP98/05360

§ 371 (c)(1),
(2), (4) Date: Jun. 22, 2000

(87) PCT Pub. No.: WO99/10528

PCT Pub. Date: Mar. 4, 1999

(30) Foreign Application Priority Data

Aug. 22, 1997 (DE) .................. 197 36 691

(51) Int. Cl.
*C07H 21/04* (2006.01)
*C12Q 1/68* (2006.01)
(52) U.S. Cl. .............. 435/6; 435/91.1; 435/91.2; 536/23.1; 536/24.3
(58) Field of Classification Search ............. 435/6; 536/23.1
See application file for complete search history.

(56) References Cited

U.S. PATENT DOCUMENTS

| | | | | |
|---|---|---|---|---|
| 5,589,579 | A * | 12/1996 | Torczynski et al. | 536/23.1 |
| 5,871,917 | A * | 2/1999 | Duffy | 435/6 |
| 5,962,237 | A * | 10/1999 | Ts'o et al. | 435/7.23 |
| 5,976,797 | A * | 11/1999 | Mitsuhashi | 435/6 |
| 6,057,105 | A * | 5/2000 | Hoon et al. | 435/6 |
| 6,190,870 | B1 * | 2/2001 | Schmitz et al. | 435/7.23 |
| 6,197,523 | B1 * | 3/2001 | Rimm et al. | 435/7.1 |

FOREIGN PATENT DOCUMENTS

WO   WO 96/17080   * 6/1996   ................ 1/68

OTHER PUBLICATIONS

Pantel et al. "Methods for detection of micrometastatic carcinoma cells in bone marrow, blood and lymph nodes" Oncology, vol. 18, p. 394-401, 1995.*
Pelkey et al "Molecular and immunological detection of circulating tumor cells and micrometastases from solid tumors" Clinical Chemistry, vol. 42, No. 9, p. 1369-1381, 1996.*
Noguchi et al "The detection of breast carcinoma micrometastases in axillary lymph nodes by means of RT-PCR" Cancer, vol. 74, No. 5, p. 1595-1600, 1994.*
Schmitz-Drager et al "Molecular biology of dissemination in bladder cancer, laboratory findings and clinical significance" World J. Urology, vol. 14, p. 190-196, 1996.*
Jung et al "Quality management and influential factors for the detection of single metastatic cancer cells by RT-PCR" Eur. J. of Clinical Chemistry and Clinical Biochemistry, vol. 35, No. 1, p. 3-10, Jan. 1997.*
Burchill et al "Detection of epithelial cancer cells in peripheral blood by RT-PCR" Br. J. of Cancer, vol. 71, p. 278-281, 1995.*
Pittman et al "RT-PCR for expression otyrosinase to identify malignant melanoma cells in peripheral blood" Annals of Oncology, vol. 7, p. 297-301, 1996.*
Zhuang et al. "Detection of the von Hippel-Lindau gene deletion in cytologic specimens using microdissection and the polymerase chain reation" ACTA cytologica, vol. 38, No. 5, p. 671-675, 1994.*
Popescu et al. "Molecular cytogenetic characterization of cancer cell alterations" Cacner Genetics and Cytogenetics, vol. 93, No. 1, p. 10-21, Jan. 1997.*
Ditkoff et al. "Detection of circulating thyroid cells in peripheral blood." Surgery. vol. 120, pp. 959-965, 1996.*

* cited by examiner

*Primary Examiner*—Jeanine A. Goldberg
(74) *Attorney, Agent, or Firm*—Bacon & Thomas, PLLC

(57) ABSTRACT

The invention relates to a diagnostic method and related compositions for characterizing disseminated and micrometastasized cancer cells in body fluids using DNA, mRNA and/or protein. According to the method, DNAs, mRNAs and/or proteins of cancerous and non-cancerous cells obtained from a body fluid (i.e., cell preparations that are not enriched for cancer cells) and DNAs, mRNAs and/or proteins of cancerous cells that are removed from the body fluid (i.e., cell preparations that are enriched for cancer cells) are analyzed, to determine the presence or expression in body fluid cells of at least one cancer-specific gene that is not expressed in non-cancer cells or of at least one cancer-associated gene, and of at least one cancer-specific or cancer-associated gene in cancer cells removed from the body fluid cells (i.e., in isolated cancer cells). Also provided are compositions and methods for testing antineoplastic substances and anticancer therapies by characterizing a cancer-specific or a cancer-associated gene, and examples of cancer-specific and cancer-associated genes, including tissue-specific genes, tumor suppressor genes, oncogenes and others.

21 Claims, No Drawings

METHOD FOR CHARACTERIZING DISSEMINATED AND MICROMETASTASIZED CANCER CELLS

The present invention relates to a method for the characterization of disseminated and micrometastasized cancer cells on the basis of RNA and/or DNA, to the use of this method for in vitro diagnosis of cancer and the use of cancer cells characterized according to the invention for testing active substances for an antineoplastic effect, and to means for carrying out the method.

The diagnosis of cancer in humans continues to represent one of the greatest challenges to present-day medicine. It is frequently possible with current diagnostic methods to identify cancerous growths, which are embraced hereinafter by the term tumours (sarcomas, carcinomas, systemic haematological malignancies), only when the tumour has already reached an advanced stage. Despite considerable advances in imaging methods, a certain minimum size of the tumour is always necessary for successful use thereof. In addition, only very little, if any, further information about the nature and constitution of the tumour can be obtained with such methods. The time-consuming and cost-intensive imaging methods are therefore usually employed merely as aids to orientation for the subsequent, frequently direct, procedure, usually removal of tissue. However, this means an invasive procedure on the patient's body which may, depending on the location and constitution of the tumour, be very unpleasant or even dangerous for the patient.

If a tumour is diagnosed on the basis of such a tissue removal, it is normal for further investigations to follow with the intention of, for example, describing the potential for spread, that is to say the formation of metastases, by this tumour. If, for example, breast cancer is diagnosed, it is usual to remove 20 to 30 lymph nodes from the patient involved and determine the number of lymph nodes having cancer cells. The prevailing opinion is that the patient's chances of survival decrease with an increasing number of lymph nodes affected. However, recent findings indicate that the occurrence of such lymph node metastases is a measure more of the age than of the aggressiveness or the metastasis potential of the tumour.

New ways of diagnosing cancer have appeared in recent years during the progressive development of methods of molecular biology and the increasing knowledge about the genetic bases of cellular degeneration. It has been assumed that cancer cells express characteristic markers, on the basis of which they ought to be distinguishable from nondegenerate cells and thus identifiable as cancer cells. The development of the hybridoma technique and the cultivation of monoclonal antibodies made possible thereby has led to the design of a large number of immunoassays intended to contribute to the diagnosis of cancer by detecting particular markers. Examples of such markers are carcinoembryonic antigen (CEA), α-fetoprotein (AFP) or prostate-specific antigen (PSA). EP 0 747 705 has recently proposed investigation only of the 90 kDa glycoform of a group of proteins (NCAs) structurally related to CEA in the blood because apparently only this glycoform is released into the bloodstream. WO 96/21862 indicates that measurement of the concentration of A-protein in the blood would allow diagnosis of cancer, but also states that the hopes placed on the markers investigated hitherto, such as CEA, AFP or PSA, have not been fulfilled. Other methods based on the immunological detection of particular proteins are described, for example, in DE 195 00 723; WO 97/26271; WO 97/28186; WO 96/01907; U.S. Pat. No. 5,633,142; U.S. Pat. No. 5,620,848; U.S. Pat. No. 5,589,579; and U.S. Pat. No. 5,563,247. However, a reliable diagnosis of cancer does not appear to be possible in this way at least at present.

Other research teams have, by contrast, concentrated on analysing the genetic material of cancer cells. Thus, WO 93/04200 proposes, for estimating a predisposition to breast cancer, isolating DNA from a sample of the patient's blood, restricting this DNA in a particular way and making an appropriate diagnosis on the basis of the restriction pattern. However, a detection of tumour cells in the blood is not possible with this method.

Furthermore, WO 96/02671 describes a method with which genomic DNA or cDNA from neoplastic tissue, blood or another body fluid is investigated, solely by sequence analysis (sequencing or hybridization), for mutations of a gene which codes for a protein whose disturbed function is thought to be connected with cancer. Similar approaches are reported in WO 97/26271; WO 97/28186; WO 96/15262; WO 96/01907; WO 93/22456; U.S. Pat. No. 5,620,848; U.S. Pat. No. 5,149,628 and WO 96/21021.

There have also been many proposals to investigate the free DNA and/or RNA present in blood plasma for oncogenic mutations or deletions, tumour suppressor gene mutations or deletions or changes in the microsatellite pattern (compare, for example, WO 95/16792; DE 37 21 400; DE 37 17 212; and WO 93/22456).

Finally, WO 94/10343 also describes a method for diagnosing cancer, namely for identifying prostate cancer micrometastases, entailing investigation of a patient's blood for RNA coding for prostate-specific antigen. However, so-called false-positive responses are obtained in about two thirds of the cases with this method, because inflammations of or injuries to the prostate gland also increase the concentration of the protein in the blood. On the other hand, because of inadequacies in the test, presumably 30% of cancers still remain undiscovered. A similar procedure is chosen in U.S. Pat. No. 5,601,990 for diagnosing metastasizing bowel cancer.

In summary, therefore, it can be stated that the prior art provides no reliable diagnosis of cancer.

The present invention is therefore based on the object of designing an in vitro method with which all types of cancer in mammals and, in particular, in humans can be identified and assessed reliably and with sufficient accuracy, also for individual patients, and which makes it possible to follow the progress of a suitable cancer therapy. The method is additionally intended to make it possible to test active substances for an antineoplastic effect.

This object is achieved according to the invention by a method for the characterization of disseminated and micrometastasized cancer cells on the basis of DNA and/or RNA, wherein cells obtained from body fluid from an individual are investigated for at least one cancer-specific gene on the basis of mRNA; and/or cancer cells removed from body fluid from an individual are investigated for at least one cancer-specific gene on the basis of DNA and/or mRNA, and the same investigation is carried out with non-cancer cells from the same individual for comparison.

Characterization means according to the invention all procedures which can be carried out on cells from mammals and, in particular, from humans in order to detect qualitatively or quantitatively one, two, three, four, five, 6 to 10, 11 to 20 or more cancer-specific and/or cancer-associated genes in these cells. It is then possible to identify the cells on the basis of the results obtained in the characterization. This embraces according to the invention not only the qualitative detection of circulating cancer cells but may also comprise quantitation thereof and/or information about their origin and behaviour, for example in relation to metastasis formation or for a wide variety of, for example, cytotoxic, therapeutic approaches.

Circulating cancer cells include, according to the invention in particular those cancer cells which have become detached from the primary tumour, that is to say disseminated and micrometastasized cancer cells. For the purpose of simplification, reference will be made hereinafter to circulating cancer cells. Because the spread of these cells is usually connected with the vascularization of the primary tumour, circulating cancer cells can be found in particular in the blood, with bone marrow and lymph nodes also being suitable. Accordingly, body fluids such as blood, lymph, urine, bone marrow and various organ irrigation fluids such as bronchial lavage, pancreatic or bladder irrigation fluid are investigated according to the invention.

A distinction is made according to the invention between cancer-specific and cancer-associated genes. Cancer-specific in the sense according to the invention are those genes on the basis of which it is possible to identify a circulating cancer cell as such. Cancer-associated genes, by contrast, are not specific for cancer cells. They may also be expressed in healthy cells or in a wide variety of other disorders, for example inflammations. However, expression thereof may be characteristically modulated in cancer cells in comparison with non-cancer cells, so that further conclusions can be drawn about the nature and the behaviour of the cancer cells.

In this sense, it is also possible, of course, that a particular gene may contribute to both the cancer-specific and the cancer-associated characterization. For example, a gene may have a mutation which leads to anomalous expression of a cell cycle-regulating protein and, as a consequence, to degeneration of the affected cell. This mutated gene is therefore cancer-specific and the investigation according to the invention for detecting this mutated gene serves for cancer-specific characterization. In addition, analysis of the anomalous expression of this gene may also contribute to the cancer-associated characterization because the nature or quantity of corresponding expression products are important for the cell cycle and thus further conclusions can be drawn about the nature and the behaviour of the cancer cells.

The investigation for cancer-specific and cancer-associated genes can be carried out in every way conceivable to the skilled person. Thus, a gene according to the invention can be investigated at the DNA level, at the RNA level and/or at the protein level. Investigation at the DNA level is preferably of genomic DNA for mutations, amplifications, LOHs, translocations and/or polymorphisms. Investigation at the RNA level and at the protein level is of expression products, namely and preferably transcription products such as mRNA and translation products such as proteins. Preferred methods are those able to assist in assessment of the involvement of a gene in the condition of circulating cells at the time of investigation, for example investigation of mRNA in particular in relation to the amount of a particular mRNA present in a cell. If the method according to the invention includes investigation of a body fluid for proteins, these are, in particular, ones expressed by the cancer-specific and/or cancer-associated genes. Unless indicated otherwise, references made hereinafter will embrace investigation or analysis of the genes according to the invention.

The specific genes mentioned in the following description are frequently referred to by abbreviations or codes which are customarily used and are therefore known to the skilled person. In addition, reference may be made to the glossary inserted at the end of the present description for explanation.

The cancer-specific genes according to the invention include, in particular, two classes of genes which play an essential part in the development of cancer: oncogenes which are produced by mutation from so-called proto-oncogenes, and mutated tumour suppressor genes. In their normal form, both direct the life cycle of a cell: proto-oncogenes promote cell growth, while tumour suppressor genes retard it. Oncogenes are cancer-favouring because they stimulate the cell to excessive proliferation, whereas tumour suppressor genes contribute to the development of cancer if they are inactivated by mutation and, as a consequence, the cell loses an inhibitor of growth by which inappropriate proliferation of it is normally prevented. Oncogenes code for example for growth factors and their receptors, signal proteins, transcription factors and a large number of other proteins, of which some, for example, play an important part in apoptosis. Oncogenes include, for example, genes such as the bcl-2 family, mdm2, c-abl, the myc family, for example c-, N-, R-, L- and B-myc, the ras family, for example H-, K- and N-ras, erb-B2, which is also called neu, erb-B, PDGF, RET and viral oncogenes of various tumour viruses such as papovaviruses, for example SV40, polyoma- and papillomaviruses such as HPV, adenoviruses, certain herpesviruses, poxviruses, hepatitis B viruses (HBx gene), hepatitis C viruses, HTLV-1, E1A fusion transcript in adenoviruses, E6 and E7 fusion transcripts in HPV and EBV in Burkitt's lymphoma.

Oncogenes preferred according to the invention are genes of the ras family, erb-B2, erb-B, c-myc, mdm2, bcl-2, hepatitis B viruses (HBx gene), hepatitis C viruses, HTLV1, E1A fusion transcript in adenoviruses, E6 and E7 fusion transcripts in HPV and EBV in Burkitt's lymphoma. Very particular preference is given to c-myc, k-ras and erb-B2.

The tumour suppressor genes include, for example, the genes of the APC family (FAP), DCC, DPC4, NF-1 NF-2, MTS1, RB, p53, WT1, BRCA1, BRCA2, VHL, MSH2, MLH1 and WAF1.

Tumour suppressor genes preferred according to the invention are p53, RB, APC, DCC, BRCA1, BRCA2, MSH2, MLH1 and WAF1. Very particular preference is given to p53, RB, APC, DCC and DPC4.

The cancer-specific genes include not only oncogenes and mutated tumour suppressor genes but also genes which are switched off, that is to say are expressed in only inconsiderable amounts, if at all, in non-cancer cells in body fluids investigated according to the invention. If, therefore, transcription and/or translation products of these genes are detected in a body fluid, for example blood, this indicates the presence of circulating cancer cells in the relevant body fluid.

These include, for example, hCG, hTG, calcitonin, albumin, surfactant proteins, telomerase, various translocations, Stat5a, variants of steroid receptors (ER, AR), progesterone receptor, various genes showing an LOH, CEA, PSM, PSA, AFP, tyrosinase, MAGE3, Muc18, MUC1, cytokeratins, in particular CK20 and CK19, LOH investigations in various chromosome sections by numerous microsatellites, gastrointestinal tract hormones such as motilin, enteroglucagon, GIP, gastrin, CCK or PYY, and neurotensin. Preference is given according to the invention to CEA, PSM, MUC1 (tumour-specific splice variants), AFP, cytokeratin, tyrosinase, MAGE3, MUC18, tumour-specific splice variants of the oestrogen and androgen receptors, and EGP.

Genes of this type also include the tissue-specific genes which are mentioned below and which, because of their tissue specificity, contribute to the cancer-associated characterization according to the invention, but can also be used, due to the specific nature of the object investigated, namely cancer cells detached from the primary tumour and circulating in a body fluid, for the cancer-specific characterization.

It is also possible to use prognostic oncoproteins, such as anti-p53, pan p53, p53 or c-erb-B2, for the cancer-specific investigation.

In a preferred embodiment of the present invention, a body fluid is investigated for at least one cancer-specific gene and at least one cancer-associated gene. For this purpose, cells obtained from body fluid from an individual are additionally investigated for at least one cancer-associated gene which is essentially not expressed in non-cancer cells in the body fluid investigated; and/or cancer cells removed from body fluid from an individual are additionally investigated for at least one cancer-associated gene and the same investigation is carried out on non-cancer cells from the same individual for comparison.

The cancer-associated genes according to the invention embrace a wide range of functions. Particularly suitable ones are tissue-specific, that is to say organotypical, genes (morphogenes) which provide information on the origin of the circulating cancer cells, so that conclusions can be drawn about the location of the primary tumour, the source of spread; genes which characterize the ability of the cancer cells to metastasize; genes which code for steroid hormone receptors, so that information can be obtained about the receptor status of the cancer cells; drug resistance genes; or genes whose expression correlates with the modulation of the immune response, and cell proliferation and apoptosis of circulating cancer cells. Expression of these cancer-associated genes may be modulated in a characteristic way in cancer cells, so that the resulting expression pattern may also point to cancer.

Cancer-associated tissue-specific genes frequently code for organotypical markers, that is to say proteins or antigens, on the basis of which conclusions can be drawn about the origin of the cell expressing the gene. These include, for example, liver-specific genes such as albumin or AFP; prostate-specific such as AR, PSM, hK2 or PSA; breast-, ovary- and/or cervix-specific, such as B-hCG, ER, PR, SCCA-1, maspin or BA46; colorectal-specific such as CCK, enteroglucagon, GIP, gastrin, motilin or PYY; pancreas-specific such as PYY; melanoma-specific such as MAGE1, MAGE3, Muc18 or tyrosinase; thyroid-specific such as hTG; lung-specific such as SF, SF-R, surfactant proteins, for example SP-A and SP-C, CC10, N-CoR or RARβ2; bladder-specific such as EGF-R and β-hCG; endometrium-specific such as SCCA.

It is also possible to have recourse to oncogenes and/or mutated tumour suppressor genes for the tissue-specific characterization if they point to particular types of cancer. Examples thereof are tumour-associated mutations such as translocation 14;18 (bcl-2) for lymphomas, translocation 9;22 (BCR/ABL) for chronic myeloid leukaemias, translocation 15;17 for acute non-lymphocytic leukaemias, translocation 2;13 (PAX3-FKHR) and translocation 1;13 (PAX7-FKHR) for alveolar rhabdo-myosarcomas, translocation 11;22 for Ewing's sarcomas, translocation 12;16 for myxoid liposarcomas, translocation x;18 for synovial sarcomas; BRCA-1 and BRCA-2 for breast carcinomas, DPC-4 for pancreatic carcinomas, erb-B for glioblastomas, MLH-1 and MSH-2 for HNPCC (hereditary nonpolyposis colon cancer), NF-2 for neurofibromatosis-1, NF-1 for neurofibromatosis, RET for thyroid carcinomas, RB for retinoblastomas, VHL for renal carcinomas, WT-1 for renal tumours, and k-ras for colon carcinomas.

Characterization of the ability of circulating cancer cells to metastasize occupies a special position according to the invention. For this purpose, the cells are investigated in particular for genes which code for angiogenesis, growth and motility factors, matrix degradation factors such as proteases and their inhibitors, or adhesion factors such as adherins.

Angiogenesis factors include, for example, aFGF and bFGF and their receptors aFGF-R and bFGF-R, VEGF and its receptors VEGF-R1 and VEGF-R2, and GD-AIF.

Growth factors include, for example, TGF-α and TGF-β, IGF, IGF-BP3, erb-B (EGF-R), PDGF and EGF.

The migration-stimulating motility factors include, for example, the scatter factor SF-L and its receptor SF-R (c-met).

Proteases and their inhibitors embrace, for example, matrix hydrolases such as MMPs (matrix metalloproteases), MT-MMP, UPA (urokinase-like plasminogen activator) or inhibitors thereof such as PAI1 and PAI2 (plasminogen activator inhibitor) or TIMPs (tissue inhibitors of metalloproteases).

The adherins include adhesion proteins such as cadherins, for example E-cadherin, catenins, for example β-catenin, selectins, for example E-, P- and L-selectin, and their receptors, CD44 (standard and splice variants), integrins and ICAMs.

Genes preferred according to the invention for characterizing the ability to metastasize are angiogenesis factors (bFGF and bFGF-R; VEGF and VEGF-Rs), proteases (UPA; PAI; MMPS; TIMPs), adherins (E-cadherin; α-catenin; β-catenin; selectin-L and -R; CD44), motility factors SF-L and c-met and metastasis suppressor nm23.

The steroid hormone receptor genes preferably used according to the invention are the genes which code for the oestrogen, progesterone or androgen receptor (ER, PR or AR).

The characterization of drug resistance genes in circulating cancer cells is also of particular importance according to the invention because cancer cells are frequently resistant to therapeutic agents, and some of them are multi-resistant, and characterization of these genes can contribute to assessing the prospects of success of particular cancer therapies. Examples of such drug resistance genes are MDR1 which codes for P-glycoprotein, and nm23, hMLH1, gp170, MRP1, the topoisomerase gene, the glutathione S-transferase pi gene, the LRP gene and genes which code for α- or β-tubulin.

Drug resistance genes preferably investigated according to the invention are MDR1, MRP1, the topoisomerase II gene, the LRP gene, the β-tubulin gene and the glutathione S-transferase pi gene.

For characterizing a modulation of the immune response it is possible, for example, to make use of assessment of the T- and NK-cell-mediated cytotoxicity and/or antibody-dependent cell-mediated cytotoxicity (ADCC). For this purpose it is possible to investigate immunological effector cells, in particular NK, H1/TH2 and CD8 cells on the one hand and circulating cancer cells on the other hand, for example for the TNF-α gene (tumour necrosis factor), genes which code for interferons, for example α- and γ-IFN, FAS ligand and FAS receptor genes, perforin1, bcl-2, bax and granzymes. FAS-R and FAS-L, perforin and granzymes are preferred.

The proliferation and apoptosis properties of circulating cancer cells are investigated according to the invention on the basis of genes which correlate with the proliferation and apoptosis status of cells, in particular cancer cells. These include, inter alia, some of the abovementioned oncogenes and proto-oncogenes and tumour suppressor genes and mutated tumour suppressor genes which may—beyond the cancer-specific characterization—also contribute to the cancer-associated characterization because of their expression pattern. Recourse is had according to the invention to, for example, p53, genes which are inactivated (bcl-2; c-myc; bFGF, c-fos; HSP70; IL-6; MDR1; PCNA) or activated (Bax; FAS-L and -R; cyclins A, B1, D1, D2, D3, E or G; GADD45; GD-AIF; HIC1; IGF-BP3; mdm2; p21) transcriptionally and sequence-specifically by p53, genes which are expressed at the start of apoptosis and of cell cycle arrest (apart from p53 also TNF-α, TNF-R1, TNF-R2, DPC-4, IFN-γ und FAS-L and -R) and genes which occur when there is unregulated growth such as erb-B2, EGF and other autocrine growth factors (TGF-α; PDGF). Preference is given to Bax, FAS, cyclins, mdm2, p21, p16, bcl-2, c-myc, FGF, MDR1, TNF-α, IFN-γ, erb-B2, EGF and other autocrine growth factors.

For tumour biological investigation, that is to say for characterizing a modulation of the immune response, the proliferation and apoptosis properties, cyclins, in particular the cyclins B1, D1 and E, Ki67, FAS-L, FAS-R, bax and/or bcl-2 are preferably investigated.

The investigation of a body fluid can take place by using known immunological methods. These include, for example, immunoprecipitation and competition experiments, immuno-fluorescence, immunohistochemical staining methods, Western blotting, flow cytometry, ELISA and the like, and mass spectrometric methods. Since immunological methods usually aim at particular antigen-antibody interactions, such methods are preferably used for investigating the body fluid for proteins, the proteins being in particular those expressed by the genes described previously. Antibodies possibly required for this purpose either are known to the skilled person or can be obtained by customary methods. Immunological methods are preferably used according to the invention for investigating blood and, in particular, bone marrow. It is possible with immunological methods in an advantageous manner to analyse the following proteins, for example: P53, ERB-B2 and tumour antigens using ELISA and similar methods; FAS ligand and FAS receptor, phosphatidylserine, cytokines, perforin, cytokeratins and cyclins with the aid of immunophenotyping.

A preferred possibility for the investigation according to the invention of body fluids is provided by nucleic acid analysis. This includes, for example, investigations of DNA or RNA, in particular mRNA, using techniques known to the skilled person, such as sequencing techniques, hybridization techniques, for example Northern or Southern blotting, hybridization on microchips, in particular methods based on the polymerase chain reaction (PCR) and also techniques in which the DNA or RNA to be investigated is firstly transcribed and/or translated in vitro. It is possible according to the invention to investigate every body fluid by means of nucleic acid analysis. Recourse is advantageously had to blood, especially when mRNA is investigated. It is, of course, also possible to employ a combination of different nucleic acid analyses to investigate a gene. A combination of immunological methods and nucleic acid analyses may also be advantageous.

Many of the cancer-specific and cancer-associated genes are preferably investigated on the basis of mRNA. A technique used for this purpose is direct hybridization of mRNA and/or cDNA (qualitatively/quantitatively) on a solid matrix (for example in the form of microchips) with immobilized oligonucleotides or immobilized streptavidin and biotinylated oligonucleotides. mRNA, cDNA or double-stranded PCR products are hybridized onto the latter. Various ways for introducing the signal are available, for example primer extension by labelled dNTP and ddNTP. The detection principle is chosen appropriate for the label: radioactivity, fluorescence, chemiluminescence or other methods known to the skilled person for this purpose.

Use is made in particular of a well-known technique which combines reverse transcription (RT) and the polymerase chain reaction (PCR) and is referred to hereinafter as RT-PCR. In this method, firstly the mRNA is isolated from the cells from a body fluid according to the invention. This is then transcribed with the aid of reverse transcriptase to cDNA which is subsequently amplified with the aid of the PCR. The PCR products obtained in this way can then be either subjected to a fragment analysis, where appropriate after suitable purification, sequenced directly or indirectly via further cloning cycles or else expressed in vitro. The investigated mRNAs are quantified via various internal controls, preferably in the form of cell equivalents or cloned cDNAs or cRNAs by fluorescence-labelled primers, by real-time PCR or by RNA hybridization on microchips. The cell-specific quantification of genes takes place via internal standards, in particular RNA (cDNA) independent of the cell type and coding, for example, for GAPDH, β-micro-globulin, L32 or β-actin. The specificity is verified by comprehensive controls such as mismatch samples or sequencing of the cDNA.

The cancer-specific genes, which are preferably characterized on the basis of mRNA analyses on body fluids, are, in particular, the genes described above which are essentially not expressed in non-cancer cells in the body fluid investigated.

Cancer-associated genes are, as a rule, preferably characterized on the basis of mRNA analyses of body fluids. These include, in particular, the following genes: bFGF, bFGF-R, VEGF, VEGF-Rs, MMPS, TIMPs, MDR1, MRP, LRP, topoisomerase II, glutathione S-transferase, progesterone receptor, Bax, bcl-2, FAS-L, FAS-R, mdm2, p21, p16, c-myc, TNF-α, IFN-γ, erb-B2 and EGF.

A DNA analysis, in particular sequence analysis of genomic DNA, is usually preferred for the investigation for oncogenes and/or mutated tumour suppressor genes and may be advantageous in particular for characterizing the following genes: p53, ras family, erb-B2, c-myc, mdm2, BRCA1, BRCA2, APC, DCC, RB MSH2, MLH1, RET and LOH investigations in various chromosome sections by numerous microsatellites.

Body fluids can be analysed in the state in which they have been obtained. However, the samples are usually according to the invention firstly prepared by procedures known per se for the subsequent investigation by obtaining cells or cell-containing concentrates or cell-containing liquids from the body fluid. This applies in particular to nucleic acid analyses. Thus, for example, in place of blood it is possible and advantageous to use certain cell-containing liquids derived therefrom or cell concentrates, for example the so-called Buffy coat or cell fractions after density centrifugation. The cells obtained from body fluid can then be investigated in particular for those genes which are essentially not expressed in non-cancer cells in the body fluid investigated.

Cancer cells removed from the body fluid are usually investigated according to the invention for investigating for genes which are also expressed by non-cancer cells in the body fluid investigated or in investigations for genomic DNA.

Known methods can be employed for removing cancer cells, for example physical methods such as microfiltration or density gradient centrifugation, or antigen-specific immunoadsorption methods in which specific antibodies label the cancer cells in such a way that they can subsequently be sorted out. Suitable antibodies (for example anti-EGP) are provided, for example, with fluorescent and, in particular, magnetic markers so that on use of a cancer cell-specific antibody labelled in this way it is possible to isolate cancer cells after binding such antibodies in so-called cell sorters. For selecting suitable antibodies for the purposes of isolating particular cancer cells it is possible to have recourse to the characterization and identification of these cancer cells without previous isolation. The state in which the cancer cells are isolated is preferably viable and, in particular, capable of proliferation. In particular, the mRNA should be intact for the investigations described above.

The cell fractions obtained after a separation must then be quantified with reference to cell-type-independent markers (for example GAPDH, $\beta$-microglobulin, L32 or $\beta$-actin). A further possible demonstration of purity is through RNA which is specific for MNCs (mononuclear cells) (perforin, CD45). The various cell fractions obtained after separation (fraction A: MNC including the tumour cells; fraction B: MNC after removal of the tumour cells; fraction C: purified tumour cells) are then also compared with one another by investigating the removed cancer cells and carrying out the same investigation with non-cancer cells from the same individual for comparison. This means that the patient's own controls are included in the investigation.

In a particular embodiment of the present invention, single cancer cells are removed from the body fluid and are also investigated singly. It is possible for this purpose to analyse an altered genome of a single degenerate cell by genome amplification by a so-called single-cell PCR.

The isolation of circulating cancer cells is advantageously carried out for genomic investigations and the investigation for genes which are also expressed by non-cancer cells in the body fluid investigated, for example the following genes: DNA: p53, ras family, erb-B2, c-myc, mdm2, RB, APC, DCC, LOH investigations in various chromosome sections by numerous microsatellites: RNA: bFGF, bFGF-R, VEGF-Rs, MMPs, TIMPs, MDR1, MRP, LRP, topoisomerase, glutathione S-transferase, Bax, bcl-2, FAS, mdm2, p21, p16, c-myc, FGF, MDR1, TNF-$\alpha$, IFN-$\gamma$ and EGF, AR, ER, EGP and SF.

Certain investigations according to the invention are preferably carried out on cell cultures. This can be done by isolating the circulating cancer cells in the manner described above and then cultivating them under suitable conditions. It is possible in particular with in vitro cultures to gain information on the tumour biology (for example the modulation of the immune response by cancer cells or the proliferation) of these cells.

Genes advantageously characterized using cancer cells cultivated in vitro are, for example, the following: Bax, FAS, cyclins, mdm2, p21, p16, bcl-2, c-myc, FGF, MDR1, TNF-$\alpha$, IFN-$\gamma$, erb-B2 and EGF.

The method according to the invention can be used irrespective of the stage of a cancer. It can be employed alone or in combination with other cancer diagnostic methods such as imaging methods or methods based on conventional tumour markers. The method according to the invention can be employed for prevention, on the appearance of the first warning signs of cancer or, for example, after a cancer therapy for early recognition of recurrence. It is suitable for the characterization and identification of all types of cancer as long as corresponding circulating cancer cells are present in the body fluids investigated. These include, for example, abdominal cancer, anal cancer, pelvic cancer, bile duct cancer, uterine cancer, endometrial cancer, brain cancer, head and neck cancer, lip cancer, mouth cancer, kidney cancer, parotid cancer, tongue cancer, inguinal cancer, soft tissue cancer, lymphomas, leukaemias, multiple leukaemias, and preferably breast carcinomas, sarcomas, ovarian carcinomas, lung carcinomas, pancreatic carcinomas, colon carcinomas, rectal carcinomas, prostate carcinomas, liver carcinomas, bladder carcinomas, gastric carcinomas, thyroid carcinomas, cervical carcinomas, endometrial carcinomas, melanomas, non-Hodgkin lymphomas and chronic myeloid leukaemias.

Use of the method according to the invention is of particular interest for lymph node-sparing types of cancer because in this case conventional methods based on the investigation of lymph nodes fail. If circulating cancer cells are detected with N0 tumours (for example a breast or colon carcinoma), specific statements about the choice of therapy are possible on the basis of the particular constellation. Thus, an adjuvant/curative therapy is preferably indicated in these cases, where appropriate with subsequent additional immunomodulatory therapy for advanced tumours.

Irrespective of whether investigation is only for cancer-specific or additionally for cancer-associated genes, it is preferred according to the invention to investigate for at least two different genes so that a method is made available according to the invention for multiple characterization of disseminated and micrometastasized cancer cells.

A first application of the method according to the invention is directed at detecting circulating cancer cells. For this purpose, the expression of cancer-specific genes is preferably measured. Multiparameter expression analyses of those genes which are switched off in non-cancer cells in the body fluid investigated are particularly preferred. These analyses may embrace up to about 40 genes. As a rule, up to about 25 genes, preferably about 2 to 10 genes and, in particular, about 3 to 7 genes are investigated. The corresponding mRNAs are preferably analysed, in particular by RT-PCR.

Particularly effective combinations comprise the CEA and CK20 genes, with analysis of the corresponding mRNAs being preferred. These combinations may, where appropriate, advantageously be supplemented by an investigation for MUC1, in which case the relation between the tumour-specific 336BP splice variant and the natural 309BP splice variant is analysed in particular. Investigations of this type can be used in particular for detecting circulating cancer cells of the carcinoma type. Preference is given in this connection to gynaecological carcinomas such as ovarian, breast or various uterine carcinomas, colon carcinomas, lung carcinomas, gastric carcinomas, thyroid carcinomas, bladder carcinomas, endometrial carcinomas, and prostate carcinomas. The investigation may take place without previous removal of the cancer cells. The MNC fraction is preferably used in blood investigations.

Further effective combinations comprise the MAGE3 and tyrosinase genes, with analysis of the corresponding mRNAs being preferred. These combinations may, where appropriate, advantageously be supplemented by an investigation for Muc18. Investigations of this type can be used in particular for detecting circulating cancer cells of the melanoma type.

The aforementioned expression analyses can be supplemented by other methods for detecting cancer-specific genes. For this purpose, investigations for oncogenes and/or mutated tumour suppressor genes are preferably initiated, it being possible to have recourse in particular to the abovementioned genes of this type which are preferred according to the invention. Analyses of this type, in particular for detecting mutations, amplifications, LOHs, translocations or polymorphisms, are advantageously carried out at the DNA level, for example by DNA sequencing or hybridization techniques, and may embrace up to about 40 genes. As a rule, up to about 20 genes, preferably about 2 to 10 genes and, in particular, about 3 to 7 genes are investigated.

Particularly effective combinations comprise the p53 and/or erb-B2 genes. In this case, p53 is preferably investigated on the basis of the corresponding cDNA for mutations and/or LOH and erb-B2 is preferably investigated at the DNA level for amplifications. These combinations may, where appropriate, advantageously be supplemented by investigations for c-myc and/or K-ras, with c-myc preferably being investigated at the DNA level for amplification and K-ras being investigated for mutations, and/or by investigations for RB, APC, DCC and/or DPC4, preferably on the basis of LOHs.

This first application can be supplemented by investigating the circulating cancer cells for genes which provide information about their origin, that is to say permit the source of spread to be localized to an organ. This can also take place in the form of multiparameter expression analyses in which organotypical morphogenes are measured. Analyses of this type may embrace up to about 36 genes. As a rule, up to about 14 genes, preferably about 1 to 8 and, in particular, 2 to 5 genes are investigated.

Particularly effective combinations comprise the maspin and/or PR genes, in particular for detecting breast carcinomas, with the corresponding mRNAs preferably being analysed. This combination can advantageously be supplemented by investigations for β-hCG and/or ER. An analogous statement applies to the detection of ovarian and cervical carcinomas, it being possible and advantageous in this case to supplement by an investigation for SCCA.

Further particularly effective combinations comprise the PSM and/or PSA genes, in particular for detecting prostate carcinomas, with the corresponding mRNAs preferably being analysed. This combination can advantageously be supplemented by investigations for hK2.

Further particularly effective combinations comprise the gastrin gene, in particular for detecting colon carcinomas, with the corresponding mRNA preferably being analysed. A combination of GIP and/or motilin also provides an effective possibility for detecting colon carcinomas.

Further particularly effective combinations comprise SP-A and SP-C, in particular for detecting lung carcinomas, with the corresponding mRNA preferably being analysed. This combination can advantageously be supplemented by investigations for βhCG.

Further particularly effective combinations comprise EGF-R and βhCG, in particular for detecting bladder carcinomas.

A further application of the method according to the invention relates to drawing up a risk profile for detected circulating cancer cells, on the basis of which a prognosis can be made. The metastasizing properties of these cancer cells are preferably assessed for this purpose.

The tumour risk potential can additionally be described by analysing mutations and amplifications and/or enhanced/diminished expression of particular genes which influence the growth behaviour of the cancer cells (for example: c-myc, c-erb-B2, c-fos, erb-B, mdm2, nm23, p16, p21).

Another important factor for estimating the risk is the sensitivity of the tumour to immunological attacks by the organism involved. Apoptosis of the target cell (tumour cell) depends on many effector mechanisms. It is an enormous advantage for a tumour to withstand these defence mechanisms. Apoptosis-relevant genes may indicate the extent to which a tumour is resistant or sensitive to attacks by defence cells, or possibly even can itself mount attacks on the effector cells (for example: perforin, granzyme, bax, bcl-2, fas, fas-L, GADD45, p53, TNF-R1, TNF-R2).

Of equally great importance is quantification of the tumour cells in the blood. It is crucial for there to be a difference in the number of circulating tumour cells before and after a surgical intervention or therapy. Quantification of the cancer cells on the basis of the cancer-specific genes indicated above with the aid of longitudinal standards provides such information.

Multiparameter expression analyses are preferred for drawing up a risk profile of this type. These may embrace up to about 50 genes. As a rule, up to about 25 genes, preferably about 2 to 15 genes and, in particular, about 4 to 12 genes are investigated.

Particularly preferred for estimating the risk is assessment of the metastasizing properties; this is preferably aimed at the ability of the cancer cells to degrade matrix and control angiogenesis. In this connection, recourse is had in particular to the abovementioned angiogenesis factors and/or proteases, and their antagonists.

Particularly effective combinations for the characterization of the metastasizing properties comprise bFGF, bFGF-R, VEGF-R1 and/or VEGF-R2, where appropriate together with VEGF, with the corresponding mRNAs preferably being investigated. These combinations may, where appropriate, be supplemented by investigations for MMPs, in particular MMP2, and/or TIMPs, in particular TIMP3, with the corresponding mRNAs preferably being investigated in this case too.

Effective combinations for tumour biological investigation comprise the FAS-L and FAS-R genes, which are preferably investigated on the basis of the corresponding mRNAs. This combination can advantageously be supplemented by investigations for cyclins, in particular cyclin B1, D1 and E, Ki67, bax and/or bcl-2.

A particular advantage of the method according to the invention is that individual risk profiles can be drawn up for individual patients. Since the method is particularly suitable for continuous use, that is to say can be repeated at any time, valuable information about the development of a cancer can be obtained for an individual patient on the basis of the change in such risk profiles. Another advantage is that it is thus unnecessary to have recourse to statistics which are generally based on inquiries in which patients with very different conditions are averaged.

A further application of the method according to the invention relates to the therapy of a detected cancer. Thus, statements can be made about the choice and monitoring of and resistance to therapy.

Questions of importance for the choice of therapy relate to the type of therapy or the choice of medication. These include, for example, decisions as to whether the therapy is to be curative or palliative, adjuvant or risk-adapted, and assessment of the efficacy of an anticancer therapy. For example, anticancer agents (cytostatics) which lead to programmed cell death (apoptosis) can be tested for their efficacy by investigating apoptosis-associated genes. Particularly suitable for this purpose is analysis of various mRNAs of the apoptosis-associated genes described above. These tests are preferably carried out on circulating cancer cells which are cultivated in vitro. It is thus unnecessary to administer any cytostatics to the patient.

The present invention therefore also relates to the use of disseminated and micrometastasized cancer cells characterized according to the invention for testing active substances for an antineoplastic effect.

It is possible in principle to assess all anticancer therapies with the method according to the invention. These include, for example, vaccines, immunomodulation, molecular therapies such as gene replacement, antisense nucleotides, ribozymes, monoclonal antibodies, MMP inhibitors and attenuated viruses, for example E1B attenuated viruses for the cytolysis of p53 wt-deficient cancer cells.

Since the method according to the invention is based on molecular biology investigations, it is outstandingly suitable for providing information concerning the choice of therapy adapted to the molecular endowment of the investigated cancer cells.

The assumption must be that a successful anticancer therapy will lead to a decrease and, in the most favourable case, to the complete disappearance of circulating cancer cells and/or to the loss of risk factors. If a type of cancer does not respond to a particular therapy, it must usually be assumed that the number of circulating cancer cells is not decreasing but, where appropriate, increasing or that the patient-specific risk is becoming greater. It is thus possible to assess the progress of a cancer and its therapy by repeated application of the method according to the invention. It is thus possible, by a time-dependent comparison, to assess the efficacy of a therapy and also identify in a simple manner resistance to particular types of therapy. The occurrence thereof may furthermore be confirmed by investigations of circulating cancer cells for drug resistance genes after administration of therapeutic agents to the patient.

Analysis of various genes which are the target of particular therapeutic agents, such as EGP (antibody against epithelial antigen), c-erb-B2 (anti-erb-B2 antibody mustard complex), MMP (anti-protease therapy), PR and ER (anti-hormone therapy), bFGF (anti-bFGF therapy) or topoisomerase II (doxorubicin inter alia) may provide information on the specific effect of the substances by direct quantification of the "target parameters". The success of a cytostatic therapy with microtubule-stabilizing taxanes (for example Taxol) can be predicted by detecting expression of the RNA of the monomeric target molecules (α- and β-tubulins), whose assembly is prevented by Taxol. Resistance of cancer cells to cytostatics (for example cisplatin) can be detected through the loss of the expression of DNA repair genes (for example hMLH1). It is furthermore possible by generating in vitro systems for the effect of a wide variety of therapeutic agents to be pretested directly on a patient's own tumour cells in order to establish in this way the best possible type of treatment.

Particularly effective combinations for assessing a drug resistance which may exist comprise the MDR1, MRP, topoisomerase II and glutathione S-transferase pi genes, while measuring the corresponding mRNAs, for example. Supplementary investigation of β-tubulin mutations and MDR1 amplification is also possible. For the MDR1 investigation, recourse is frequently also had to analysis of the MDR1 pump gp170 and/or the MDR1 efflux doxorubicin test.

A particular advantage of the method according to the invention is that therapy-refractory cells (minimal residual disease; MRD) can be characterized and identified and, based on this, a therapeutic approach which has already been implemented can be extended in a risk-adapted manner to eliminate completely the residual cancer cells.

Although the method according to the invention has primarily been described with reference to the characterization of human genes, it is not intended to be restricted thereto. On the contrary, a number of other applications are evident to the skilled person, such as those in animal models to answer questions which correspond or are at least similar to those above.

The present invention also relates to means for carrying out the method according to the invention. Such means should be as easy as possible to manipulate and be essentially ready for use. Means for carrying out the method according to the invention are advantageously used in kit form, for example as test kit and/or diagnostic kit. A kit of this type comprises at least one compartment, for example a vial or test tube, in which the means for the investigation according to the invention for the above genes are present where possible in aliquoted amounts. The kit normally comprises a plurality of compartments, it being possible for one compartment to be assigned to the investigation for a particular gene, but may also comprise means which can be used to investigate the plurality of genes. In some circumstances, it is also possible for a plurality of compartments to be assigned to the investigation for a particular gene. The kit also comprises, where appropriate, another compartment to receive the sample of body fluid. Contact of the sample of body fluid with the means for carrying out the method according to the invention can take place, where appropriate, in a further compartment. The choice of the means depends on the genes investigated and the method chosen.

Diagnostic and/or test kits according to the invention may comprise means for preparing the sample of body fluid, for example means for concentrating cells from body fluids, such as density gradients and/or filters, means for isolating and purifying DNA and/or RNA from cells, in particular systems based on guanidine isothiocyanate, spin columns with suitable solid phases and/or oligo-dT systems; means for carrying out reverse transcription (RT), for example reverse transcriptase, RT buffer, RNase inhibitor, suitable primers and/or dNTPs; means for carrying out the PCR, for example thermostable polymerase, PCR buffer, $MgCl_2$ and/or dNTPs; means for carrying out restriction enzyme digestions (RD), for example restriction enzyme and RD buffer; and/or means for analysing the products obtained from RT, PCR and/or RD, for example gels or means for preparing appropriate gels, ELISAs and the like.

On the other hand, many of the means necessary for carrying out the above methods are also commercially available, often even in kit form, so that merely supplementary means are necessary for carrying out the method according to the invention. Supplementary kits according to the invention of this type preferably provide appropriate primers, probes and/or negative/positive controls and, where appropriate, further aids.

Preferred kits and supplementary kits according to the invention are those which make it possible to investigate for the gene combinations which have been described above and have emerged as effective. Kits of this type are used with the aim of detecting cancer in general, localizing primary tumours, carrying out an assessment of the risks and prognosis, or gaining information in relation to therapy. Kits of this type can be combined in a type of modular system for comprehensive assessment of a cancer.

On the other hand, kits according to the invention may also comprise means making investigations possible for genes for cancer-specific and cancer-associated characterization of a particular type of cancer. For example, a melanoma-specific kit may comprise at least means for investigating for tyrosinase and bFGF, a colon-specific kit may comprise at least means for investigating for CK20, bFGF and MMP2 and a breast-specific kit may comprise at least means for investigating for CK19, bFGF, MMP2 and PR.

The following examples are intended to explain the invention in detail without restricting it.

REFERENCE EXAMPLE 1

Isolation of Mononuclear Cells (MNC) from Blood

A centrifuge tube (50 ml) is charged with 15 ml of density gradient medium (DGM) 1.077 (RT) which is cautiously overlaid with 30 ml of blood/PBS (heparinized or EDTA blood). After centrifugation (800 g, RT) for 30 minutes, all interphase cells (MNC) are transferred with a Pasteur pipette into a new centrifuge tube (15 ml) charged with 6 ml of PBS/add (PBS+BSA 0.2%, sodium azide 0.02%, EDTA 1 mM). From here on, all the steps are carried out cold (4° C.). Centrifugation (600 g, 4° C., 10 min) is followed by taking up the cells in 10 ml of PBS/add, and the cell count is determined by Trypan blue staining (95 μl of TB solution +5 μl of cell solution) (cell count=cell count from 16 small squares (Neubauer)×2×10$^6$). Centrifugation (400 g, 4° C., 10 min) is followed by the cells being taken up in ice-cold PBS/add and transferred into an Eppendorf tube (1.5 ml) (with a cell count of up to 2.5 E7 in 0.5 ml; with 2.5 E7 to 5E7 in 1 ml). Then, for RNA/DNA isolation, fraction A (¼ vol. with 20 ml, ⅙ vol. with 30 ml) is removed, the cells present therein are centrifuged (400 g, 3 min), and the resulting pellet is resuspended in 600 μl of RLT-Me buffer (from RNEasy Blood Kit Qiagen) and stored at −80° C. Finally, 10% strength FC blocking reagent is added.

REFERENCE EXAMPLE 2

Isolation of Epithelial Tumour Cells from Whole Blood

Anti-epithelial beads (40 μl/0.5 ml) are washed twice with 800 μl of PBS/add in a magnetic strip. 40 μl/0.5 ml of washed beads are placed in an Eppendorf tube, the tube is rotated in a rotor at 4° C. for 25 min and then placed in a tube stand, and the suspension from the tube lead is put into the tube. The tube is placed in an MPC for 1 min, the cell suspension is discarded, the magnetic strip is removed (or the tube is taken out) and addition of 800 μl of PBS/add is followed by cautious resuspension. The last sequence of steps is repeated 6 times, finally resuspended in PBS/1 mM EDTA (without BSA). The tube is placed in an MPC for 1 min, and the supernatant is completely removed. The resulting beads with adherent cells form fraction C. For RNA/DNA isolation, this is resuspended in 200 μl of Trizol and stored at −80° C. Perforin mRNA can be measured as a purity marker for fraction C. Evaluation takes place by determining tumour-associated and tumour-specific RNA, and determining the RNA of the epithelial glycoprotein by quantifying the GAPDH RNA.

REFERENCE EXAMPLE 3

DNA/RNA Isolation

The DNA/RNA isolation is carried out in a manner known per se.

REFERENCE EXAMPLE 4

CK20 and CEA mRNA Analysis by RT-PCR

To detect epithelial cells in blood, the content of CK20 mRNA is determined organ-selectively (ovary, colon> breast) by molecular biological means with a sensitivity of more than one cell per 106 leukocytes. The CEA mRNA content is additionally investigated. This detection of cells which form the oncogenic adherin CEA was carried out with a sensitivity of one cancer cell per 106 leukocytes.

Outline of experiment

Reverse transcription (RT):

The following reagents are mixed (RT mix):

2.35 μl of $H_2O$

4 μl of 5× first strand buffer

2 μl of 0.1 M DTT 0.15 μl of RNA guard (38950 U/ml)

0.5 μl of random primer (500 μg/ml)

0.5 μl of dNTP mix (20 mM each)

0.5 μl of M-MLV (200 U/μl)

10 μl of RNA (about 1 μg) isolated from mononuclear cells (5 ml of blood) are denatured at 70° C. for 1 min, immediately cooled on ice for 3 min, mixed free of air bubbles with 10 μl of RT mix, incubated at 37° C. for 60 min, incubated at 95° C. for 3 min, immediately cooled on ice for 3 min and either subjected directly to PCR or frozen at −20° C.

PCR:

The following reagents are mixed per PCR mixture (μl):

|  | CK20 | CEA |
|---|---|---|
| TaqMan buffer (10x) | 5.0 | 5.0 |
| $MgCl_2$ (25 mM) | 8.0 | 8.0 |
| dNTP (0.75 μl; 2.5 mM each) | 3.0 | 3.0 |
| Primer A (20 pmol/μl) | 0.75 | 0.75 |
| Primer B (20 pmol/μl) | 0.75 | 0.75 |
| TaqMan probe (20 pmol/μl) | 0.5 | 0.5 |
| Amplitaq-Gold (PE 5U/μl) | 0.5 | 0.5 |
| $H_2O$ | 28.5 | 28.5 |
| cDNA from RT | 3.0 | 3.0 |

The PCR is carried out in the ABI 7700 sequence detector (TaqMan). A two-stage PCR method is used. The following temperature profile is utilized: for CK20:

| for CK20: | |
|---|---|
| 95° C. | 12 min (hot start activation) |
| 95° C. | 30 sec |
| 57° C.* | 60 sec 45x |
| 20° C. | ∞ |
| for CEA: | |
| 95° C. | 12 min (hot start activation) |
| 95° C. | 30 sec |
| 58° C.* | 60 sec 45x |
| 20° C. | ∞ |

| Controls: | |
|---|---|
| Pos. (CK20): | NCI-H508 adenocarcinoma cell line |
| Neg. (CK20): | MES-SA/Dx5 uterine sarcoma cell line; lymphocytes from a normal donor |
| Pos. (CEA): | NCI-H508 adenocarcinoma cell line; MCF7 breast carcinoma cell line |
| Neg. (CEA): | Lymphocytes from a normal donor |

| | Primer: | | |
|---|---|---|---|
| | Primer A | Primer B | TaqMan probe |
| CK20 | CK20 sense | CK20 antisense | CK20 probe |
| CEA | CEA sense | CEA antisense | CEA probe |

Analysis of the PCR Products:

The yield from the PCR taking place is measured on line in the sequence detector for each round of cycles. The curve recorded for the progress of the reaction serves as basis for determining the amount of the cDNA to be analysed as equivalent of the mRNA. This is based on determination of when the PCR changes to the exponential phase.

REFERENCE EXAMPLE 5

MUC1 mRNA Analysis by RT-PCR

The MUC1 mRNA is determined in order to assess the carcinoma-specific mucin transcription.

Outline of Experiment

Reverse transcription (RT):

The following reagents are mixed (RT mix):

4 µl of 25 mM $MgCl_2$

2 µl of PCR buffer II (10×)

2 µl of 10 mM dCTP

2 µl of 10 mM dGTP

2 µl of 10 mM dATP

2 µl of 10 mM dTTP

1 µl of RNAse inhibitor (2000 U)

1 µl of M-MLV (5000 U)

1 µl of random hexamers (5 nmol)

5 µl of RNA (about 1 µg) isolated from mononuclear cells (5 ml of blood) are added to the RT mix and incubated at room temperature for 10 min, at 42° C. for 15 min, at 99° C. for 5 min and at 5° C. for 5 min.

The following reagents are mixed per PCR mixture (µl):

| | MUC1 |
|---|---|
| PCR buffer II (10x) | 8.0 |
| $MgCl_2$ (25 mM) | 4.0 |
| Primer A (20 pmol/µl) | 2.0 |
| Primer B (20 pmol/µl) | 2.0 |
| Amplitaq-Gold (PE 5U/µl) | 0.75 |
| $H_2O$ | 63.5 |
| cDNA from RT | 22.0 |

The PCR is carried out in a Perkin Elmer 9600 or 2400 thermocycler. The following temperature profile is used:

| 95° C. | 10 min | |
|---|---|---|
| 95° C. | 15 sec | |
| 60° C. | 30 sec | 35 cycles |
| 72° C. | 7 min | |

The PCR mixture is cooled to 4° C.

| Controls: | |
|---|---|
| Pos.: | MES-SA/Dx 5 (uterine sarcoma cell line); expresses only 336 bp splice variant |
| Neg.: | Lymphocytes from a normal donor; express only 309 bp splice variant |

| | Primers: | |
|---|---|---|
| | Primer A | Primer B |
| MUC1 | MUC S1 sense (5'-6-FAM) | MUC S2 antisense |

Analysis of the PCR Products:

12 µl of formamide, 0.5 µl of Genescan Tamra 500 (PE) and 1 µl of PCR mixture are mixed, denatured at 95° C. for 3 min, incubated on ice and analysed in an ABI Genescan 310 (anode buffer: 2% polymer, 1× genetic analyser buffer; cathode buffer: 3% polymer, 40% urea, 1× genetic analyser buffer; injection time: 10 s; injection voltage: 7 kV; run voltage: 13 kV; run temperature: 30° C.; running time: 18 min; module: Short Denatured C).

The peak areas for the PCR products (336 bp and 309 bp) are determined for the evaluation. The quotient of the peak areas for the 336 bp splice variant and the 309 bp splice variant is formed (0.2 is normal, up to 0.7 corresponds to weak expression and >0.7 to strong expression).

REFERENCE EXAMPLE 6

GST pi, FAS-R, FAS-L, MMP-2 mRNA Analysis by RT-PCR

Outline of experiment:

The reverse transcription (RT) is carried out as in Reference Example 4.

The following reagents are mixed per PCR mixture (µl):

| | GST pi | FAS-R | FAS-L | MMP-2 |
|---|---|---|---|---|
| PCR buffer II (10x) | 5.0 | 5.0 | 5.0 | 5.0 |
| ROX TIB-MOLBIOL (100 µM) | 0.75 | 0.5 | 0.5 | 0.5 |

-continued

|  | GST pi | FAS-R | FAS-L | MMP-2 |
|---|---|---|---|---|
| MgCl$_2$ (25 mM) | 6.0 | 8.0 | 8.0 | 8.0 |
| dNTP (0.75 µl each) 2.5 mM | 3.0 | 3.0 | 3.0 | 3.0 |
| Primer A (20 pmol/µl) | 1.0 | 1.0 | 0.75 | 0.75 |
| Primer B (20 pmol/µl) | 1.0 | 1.0 | 0.75 | 0.75 |
| TaqMan probe (20 pmol/µl) | 0.5 | 0.3 | 0.5 | 0.5 |
| Amplitaq-Gold (PE 5U/µl) | 0.5 | 0.5 | 0.5 | 0.5 |
| H$_2$O | 29.25 | 27.7 | 28.0 | 28.0 |
| cDNA from RT | 3.0 | 3.0 | 3.0 | 3.0 |

The PCR is carried out in an ABI 7700 sequence detector (TaqMan). A two-stage PCR method is used. The following temperature profile is utilized: for GST pi:

for GST pi:

95° C. 10 min (hot start activation)
95° C. 30 sec
57° C. 60 sec 40 ×
20° C. ∞
for FAS-R and FAS-L:

95° C. 12 min (hot start activation)
95° C. 30 sec
55° C. 30 sec 45 ×
20° C. ∞
for MMP-2:

95° C. 10 min (hot start activation)
95° C. 30 sec
58° C. 60 sec 45 ×
20° C. ∞
Number of cycles: (45 for FAS; MMP-2)

Controls:

| Pos. (GST pi): | MES |
|---|---|
| MNC (GST pi): | The limit for normal expression is fixed using the value for CT for the MNC control. |
| Pos. (FAS-R): | MNCs (normal donor); ES-2; MNC cDNA serial dilutions |
| Neg. (FAS-R): | dist. H$_2$O |
| Pos. (FAS-L): | MNCs (normal donor); ES-2; MNC cDNA serial dilutions |
| Neg. (FAS-L): | MCF-7 (breast carcinoma); Daudi (Burkitt's lymphoma) |
| Pos. (MMP-2): | COLO-320 |
| Neg. (MMP-2): | SW403; lymphocytes from a normal donor |

Primers:

|  | Primer A | Primer B | TaqMan probe |
|---|---|---|---|
| GST pi | GST pi sense | GST pi antisense | GST pi probe |
| FAS-R | FAS-R sense | FAS-R antisense | FAS-R probe |
| FAS-L | FAS-L sense | FAS-L antisense | FAS-L probe |
| MMP-2 | MMP-2 sense | MMP-2 antisense | MMP-2 probe |

Primer and probe sequences for FAS were designed in accordance with GenBank Accession # M67454; primer and probe sequences for FAS-L were designed in accordance with GenBank Accession # U08137.

Analysis of the PCR Products:
In analogy to Reference Example 4.

REFERENCE EXAMPLE 7 bFGF-R, bFGF, VEGF-R2 mRNA Analysis by RT-PCR

Outline of experiment:

The reverse transcription (RT) is carried out as in Reference Example 1.

The following reagents are mixed per PCR mixture (µl):

|  | bFGF-R | bFGF | VEGF-R2 |
|---|---|---|---|
| PCR buffer (10×) | 5.0 | 5.0 | 5.0 |
| dNTP (20 mM) | 0.5 | 0.5 | 0.5 |
| Primer A (20 pmol/µl) | 1 | 1 | 1 |
| Primer B (20 pmol/µl) | 1 | 1 | 1 |
| Taq polymerase (PE 5 U/µl) | 0.25 | 0.25 | 0.25 |
| H$_2$O | 31.55 | 31.55 | 31.55 |
| cDNA from RT | 5.0 | 5.0 | 5.0 |

The PCR is carried out in a Perkin Elmer 9600 or 2400 thermocycler. The following temperature profile is used:

95° C. 5 min
95° C. 60 sec
53° C. 60 sec
72° C. 60 sec 45 ×
72° C. 10 min

The PCR mixture is cooled to 4° C.

Controls:

| Pos. (bFGF-R): | ES-2 (ovarian carcinoma); NB-4 (ApML); MCF-7 (breast carcinoma); 697 (cALL); Colo 829 (melanoma) |
|---|---|
| Neg. (bFGF-R): | Lymphocytes (normal donor); NCI-H508 (adenocarcinoma); K562 (CML) |
| Pos. (bFGF): | ES-2 (ovarian carcinoma); K562 (CML); MES-SA/Dx5 (uterine sarcoma); Colo 829 (melanoma) |
| Neg. (bFGF): | Lymphocytes (normal donor); 697 (cALL); NCI-H508 (adenocarcinoma) |
| Pos. (VEGF-R2): | ES-2 (ovarian carcinoma); Colo 829 (melanoma); EFM192A (breast carcinoma) |
| Neg. (VEGF-R2): | Lymphocytes (normal donor); NCI-H508 (adenocarcinoma) |

Primers:

|  | Primer A | Primer B |
|---|---|---|
| bFGF-R | bFGF-R sense | bFGF-R antisense |
| bFGF-L | bFGF-L sense | bFGF-L antisense |
| VEGF-R2 | VEGF-R2 sense | VEGF-R2 antisense |

Analysis of the PCR Products a) 20–30 µl of the PCR mixture are fractionated on a 2% agarose gel (1×TBE).

b) 6–10 µl of the PCR product are incubated with (+) or without (−) restriction enzyme at 37° C. for 1 hour. After fractionation in a 2% agarose gel, two smaller fragments are to be seen.

| Restriction | + | − |
|---|---|---|
| Reagents | 6 (10) µl PCR product | 6 (10) µl PCR product |
| | 0.5 µl R enzyme | — |
| | 1 (1.5) µl buffer M | 1 (1.5) µl buffer M |
| | 2.5 (3) µl dist. H$_2$O | 3 (3.5) µl dist. H$_2$O |

REFERENCE EXAMPLE 8

Tyrosinase mRNA Analysis by RT-PCR

Outline of experiment:

The reverse transcription (RT) is carried out as in Reference Example 1.

The following reagents are mixed per PCR mixture (µl):

| | 1st round | 2nd round |
|---|---|---|
| PCR buffer (10×) | 5.0 | 5.0 |
| MgCl$_2$ (0.1 M) | 0.8 | 0.8 |
| Triton X-100 (1%) | 5.0 | 5.0 |
| dNTP (20 mM) | 0.5 | 0.5 |
| Primer A (20 pmol/µl) | 7.5 | — |
| Primer B (20 pmol/µl) | 7.5 | — |
| Primer C (20 pmol/µl) | — | 7.5 |
| Primer D (20 pmol/µl) | — | 7.5 |
| Taq polymerase (5 U/µl) + Taq antibody 1:1 | 1.0 | 1.0 |
| H$_2$O | 20.7 | 20.7 |
| cDNA from RT | 2.0 | — |
| PCR product from 1st round | — | 2.0* |

*Dilute positive control 100-fold

The PCR is carried out in a Perkin Elmer 9600 or 2400 thermocycler. The following temperature profile is used:

| |
|---|
| 95° C. 10 min |
| 95° C. 60 sec |
| 60° C. 30 sec |
| 72° C. 60 sec 30 × |
| 72° C. 10 min |

The PCR mixture is cooled to 4° C.

| Controls: | |
|---|---|
| Pos. (tyrosinase): | COLO-829 cDNA (human melanoma); 697 cDNA (pre-B-cell leukaemia) |
| Neg. (tyrosinase): | Premix without sample DNA (obligatory); MES (uterine sarcoma); LNCAP (prostate carcinoma) |

| | Primers: | | | |
|---|---|---|---|---|
| | Primer A | Primer B | Primer C | Primer D |
| Tyrosinase | HTYR-1 | HTYR-2 | HTYR-3 | HTYR-4 |

Analysis of the PCR Products:

10 µl of PCR product and 1.1 µl of sample buffer are subjected together with 10 µl of 100 bp ladder to an agarose gel electrophoresis with a run voltage of 150 volts and a running time of 20 min. Evaluation takes place under a UV lamp at 254 nm or 312 nm.

The PCR product after the 1st round has a size of 284 bp.
The PCR product after the 2nd round has a size of 207 bp.
The 100 bp ladder is used as length standard.

REFERENCE EXAMPLE 9 erb-B2, c-myc and mdr1 Amplification Analysis

The erb-B2, c-myc and mdr1 genes and the β-globin gene are coamplified using fluorescein-labelled oligonucleotide primers. The amplicons are fractionated by capillary electrophoresis.

Outline of experiment:

The following reagents are mixed per PCR mixture (µl):

| | erb-B2 | c-myc | mdr1 |
|---|---|---|---|
| PCR buffer (10×, PE) | 5.0 | 5.0 | 5.0 |
| MgCl$_2$ (25 mM, PE) | 4.0 | 4.0 | 0.5 |
| dNTP (20 mM) | 0.25 | 0.25 | 0.25 |
| (NH$_4$)$_2$SO$_4$ (100 mM) | 7.5 | 7.5 | 7.5 |
| Primer A (20 pmol/µl) | 1.5 | 2.0 | 5.0 |
| Primer B (20 pmol/µl) | 1.5 | 2.0 | 5.0 |
| Primer C (20 pmol/µl) | 0.5 | 0.2 | 0.5 |
| Primer D (20 pmol/µl) | 0.5 | 0.2 | 0.5 |
| Amplitaq-Gold (PE, 5 U/µl) | 0.4 | 0.4 | 0.25 |
| H$_2$O (double-distilled) | 25.85 | 25.45 | 23.5 |
| DNA | 3.0 | 3.0 | 2.0 |

The PCR is carried out in a Perkin Elmer 2400, 9600 or 9700 thermocycler. The following temperature profile is used:

| |
|---|
| for erb-B2 and c-myc: |
| 95° C. 10 min |
| 95° C. 1 min |
| 60° C. 1 min |
| 72° C. 1 min 32 × |
| 72 C. 3 min |
| for mdr1: |
| 94° C. 5 min |
| 95° C. 1 min |
| 57° C. 1 min |
| 72° C. 1 min 35 × |
| 72° C. 5 min |

The PCR mixture is cooled to 4° C.

Controls:

Pos. (erb-B2): DNA-A

Norm. (erb-B2): human DNA

Pos. (c-myc): DNA-B; H82-DNA

Norm. (c-myc): human DNA

Pos. (mdr1): CCRF-DNA

Norm. (mdr1): human DNA

| | Primers: | | | |
|---|---|---|---|---|
| | Primer A | Primer B | Primer C | Primer D |
| erb-B2 | Hex-neu-3 | neu-5 | PCO-3F | PCO-4 |
| c-myc | Hex-myc-1 | myc-2 | PCO-3F | PCO-4 |
| mdr1 | Hex-mdr1-5F | mdr1-5B | PCO-3F | PCO-4 |

Analysis of the PCR Products:

The PCR products are loaded onto a 2% agarose gel. After the capillary electrophoresis (Genetic-Analyzer ABI 310), the quotient of the area integral for erb-B2, c-myc or mdr1 and the area integral for β-globin is formed for each patient's sample and the controls. There is erb-B2, c-myc or mdr1 amplification in a patient's sample if the quotient is "significantly" larger than that of the normal control or of samples measured at the same time.

REFERENCE EXAMPLE 10

DCC, APC, RB, p53, microsatellite (DxSy) LOH analyses

Outline of experiment:

The following reagents are mixed per PCR mixture (μl):

| | DCC | APC | RB | p53 | DxSy |
|---|---|---|---|---|---|
| PCR buffer (10×) | 5.0 | 5.0 | 5.0 | 5.0 | 3.0 |
| dNTP mix (20 mM; 10 mM for DxSy) | 0.5 | 0.5 | 0.5 | 0.5 | 4.8 |
| MgCl$_2$ (25 mM) | — | — | — | 3.0 | 3.0 |
| Primer A (20 pmol/μl) | 0.5 | 0.5 | 0.5 | 0.5 | 0.6 |
| Primer B (20 pmol/μl) | 0.5 | 0.5 | 0.5 | 0.5 | 0.6 |
| Taq polymerase (5 U/μl) + Taq antibody 1:1 | 0.5 | 0.5 | 0.5 | 0.5** | 0.3** |
| H$_2$O | 40.0 | 40.0 | 40.0 | 37.0 | 14.7 |
| DNA* | 3.0 | 3.0 | 3.0 | 3.0 | 3.0 |

*3 μl of DNA (fraction C; tumour cell fraction; smear) 1 μl of DNA (fraction A) + 2 μl of H$_2$O
**Taq polymerase Amplitaq Gold The PCR is carried out in a Perkin Elmer 9600 or 2400 thermocycler. The following temperature profile is used:

| For DCC, APC and RB: | | |
|---|---|---|
| 95° C. | 5 min | |
| 94° C. | 30 sec | |
| 53° C. | 30 sec | |
| 72° C. | 30 sec | 30 × |
| 72° C. | 5 min | |

| For p53: | | |
|---|---|---|
| 94° C. | 10 min | |
| 94° C. | 30 sec | |
| 60° C. | 30 sec | |
| 72° C. | 30 sec | 40 × |
| 72° C. | 5 min | |

| For DxSy: | | |
|---|---|---|
| 95° C. | 10 min | |
| 94° C. | 1 min | |
| 60° C. | 30 sec | (D17S849 / D19S960) |
| 53° C. | 30 sec | (D16S265 / D11S528) |
| 57° C. | 30 sec | (D17S926 / D17S960) |
| 72° C. | 30 sec | 40 × |
| 72° C. | 10 min | |

The PCR mixture is cooled to 4° C.

Controls:

Neg.: Mixture without DNA

| | Primers: | |
|---|---|---|
| | Primer A | Primer B |
| DCC-LOH | Hex-DCC LOH-1 | DCC LOH-2 |
| RB-LOH | FAM-RB LOH-1 | RB LOH-2 |
| APC-LOH | FAM-APC LOH-1 | APC LOH-2 |
| p53-LOH | FAM-p53 LOH-A | p53 LOH-B |
| D17S926-LOH | FAM-D17S926 a | D17S926 s |
| D17S695-LOH | FAM-D17S695 a | D17S695 s |
| D17S849-LOH | FAM-D17S849 a | D17S849 s |
| D17S960-LOH | FAM-D17S960 a | D17S960 s |
| D16S265-LOH | FAM-D16S265 a | D16S265 s |
| D11S528-LOH | FAM-D11S528 a | D11S528 s |

Analysis of the PCR Products:

1. PCR Function Detection in an Agarose Gel

9 μl (15 μl for DxSy) of PCR product and 1 μl (2 μl) of 10× TBE sample buffer with bromophenol blue are loaded onto a 2% agarose gel (10 μl of ethidium bromide stock solution 10 mg/ml per 100 ml of gel) in 1× TBE buffer. The electrophoresis is carried out at a constant voltage of 160 to 170 V.

2. Detection of Allele Loss Using an ABI 310

12 μl of formamide, 1 μl of sample and 0.5 μl of Genescan Tamra 500 (PE) are denatured at 95° C. for 2 min and immediately placed on ice. A fragment analysis is then carried out in an ABI 310 (analysis buffer; anode and cathode: 1× fragment analysis buffer (PE) with EDTA; polymer: POP-4; injection time: 5 sec; injection voltage: 15 kV; voltage during the run: 15 kV; temperature during the run: 60° C.; running time: 24 min; matrix: GS POP4C).

The analysis is carried out both in whole blood, which reflects the ratio of alleles in normal cells, and in fraction C which representatively indicates the condition of the cancer cells. Successful analysis is possible only if the patient is heterozygous for both alleles of a marker. The alleles differ in size by at least 4 bp. The quotients of the peak areas for the two alleles (allele 1/allele 2) in the whole blood fraction are compared with those for fraction C. If the values differ by at least 50%, an LOH can be assumed.

REFERENCE EXAMPLE 11 p53 and K-ras Mutation Analyses

Outline of Experiment:

The following reagents are mixed per PCR mixture (μl):

|  | Cod. 175 | Cod. 245 | Cod. 248 | Cod. 249 | Cod. 273 | k-ras |
|---|---|---|---|---|---|---|
| PCR buffer (10x) | 5.0 | 5.0 | 5.0 | 5.0 | 5.0 | 5.0 |
| dNTP mix (20 mM) | 0.5 | 0.5 | 0.5 | 0.5 | 0.5 | 0.5 |
| DMSO | — | — | 2.5 | 2.5 | — | — |
| $MgCl_2$ (25 mM) | — | — | — | — | — | 6.0 |
| Primer A (20 pmol/μl) | 1.0 | 1.0 | 1.0 | 1.0 | 1.0 | 1.0 |
| Primer B (20 pmol/μl) | 1.0 | 1.0 | 1.0 | 1.0 | 1.0 | 1.0 |
| Taq polymerase (5 U/μl) + Taq antibody 1:1 | 0.5 | 0.5 | 0.5 | 0.5 | 0.5 | 0.5 |
| $H_2O$ | 37.0 | 37.0 | 34.5 | 34.5 | 37.0 | 31.0 |
| DNA | 5.0 | 3.0 | 5.0 | 5.0 | 3.0 | 5.0 |

The PCR is carried out in a Perkin Elmer 9600 or 2400 thermocycler. The following temperature profile is used:

| 95° C. | 5 min | |
| 94° C. | 30 sec | |
| 55° C. | 30 sec | |
| 72° C. | 30 sec | 37 (for k-ras 35) x |
| 72° C. | 5 min | |

The PCR mixture is cooled to 4° C.

Controls:

| Pos. (p53; 248): | DNA of acute promyelocytic leukaemia cell line NB-4; DNA of colon carcinoma cell lines Colo 320 |
| Pos. (p53; 273): | SW480 colon carcinoma cells |
| Pos. (K-ras): | SW480 and SW403 colon carcinoma cells |
| Neg. (p53): | Mixture without DNA; mixture without restriction |
| Neg. (K-ras): | Normal lymphocyte DNA or DNA of a negative cell line |

Primers:

|  | Primer A | Primer B |
|---|---|---|
| p53 (175) | FAM-p53 175-S | p53 6-2 |
| p53 (245) | FAM-p53 245-A | p53 245-S |
| p53 (248) | FAM-p53 7-1 | p53 8-2 |
| p53 (249) | FAM-p53 7-1 | p53 8-2TET-p53 8-2 |
| p53 (273) | p53 273-S | TET-p53 8-2 |
| k-ras | k-ras sense | FAM-labelled K-105 antisense |

Analysis of the PCR Products:

1. PCR Function Detection in an Agarose Gel

9 μl of PCR product and 1 μl of 10x TBE sample buffer with bromophenol blue are loaded onto a 2% agarose gel (10 μl of ethidium bromide stock solution 10 mg/ml per 100 ml of gel) in 1x TBE buffer. The electrophoresis is carried out at a constant voltage of 160 to 170 V.

2. Restriction Digestion 7.3 μl of $H_2O$ (double-distilled), 2.0 μl of 10x buffer, 0.2 μl of 100xBSA, 0.5 μl of restriction enzyme and 10 μl of PCR product (for codon 245, 249 and 273: 7.5 μl of $H_2O$ (double-distilled), 2.0 μl of 10x buffer, 0.5 μl of restriction enzyme and 10 μl of PCR product; for codon 248: 7.75 μl of $H_2O$ (double distilled), 2.0 μl of 10x buffer, 0.25 μl of restriction enzyme and 10 μl of PCR product) are incubated at 37° C. for 1 hour.

Depending on the amount of the PCR product, a 4% MetaPhor gel or an ABI 310 is used for the evaluation.

Evaluation Using MetaPhor Agarose Gel:

18 μl of restricted PCR product and 2 μl of 10 x TBE sample buffer with bromophenol blue are loaded onto a 4% MetaPhor agarose gel (10 μl of ethidium bromide stock solution 10 mg/ml per 100 ml of gel) in 1xTBE buffer. The electrophoresis is carried out at a constant voltage of 160 to 170 V. For comparison, the uncut PCR product from an arbitrary sample is also loaded onto each gel.

Detection Using an ABI 310

12 μl of formamide, 1 μl of sample and 0.5 μl of Genescan Tamra 500 (PE) are denatured at 95° C. for 2 min and immediately placed on ice. A fragment analysis is then carried out in an ABI 310 (analysis buffer; anode and cathode: 1x fragment analysis buffer (PE) with EDTA; polymer: POP-4; injection time: 5 sec; injection voltage: 15 kV; voltage during the run: 15 kV; temperature during the run: 60° C.; running time: 24 min; matrix: GS POP4C).

Fragment lengths:

| Codon 175 | | | |
|---|---|---|---|
| Wild type: | 70 bp | 227 bp | 18 bp |
| Mutated: | 88 bp | 227 bp | |
| Codon 245 | | | |
| Wild type: | 145 bp | 23 bp | |
| Mutated: | 168 bp | | |
| Codon 248 | | | |
| Wild type: | 77 bp | | |
| Mutated: | 246 bp | | |
| Codon 249 | | | |
| Genotype: | | | |
| Wild type: | 81 bp | | |
| Mutated: | 147 bp | | |
| Codon 273 | | | |
| Wild type: | 116 bp | 21 bp | |
| Mutated: | 137 bp | | |
| K-ras codon 12 | | | |
| Wild type: | 114 bp | 29 bp | 14 bp |
| Mutated: | 143 bp | 14 bp | |

For the evaluation, the 88 bp to 70 bp, 168 bp to 145 bp, 246 bp to 77 bp, 147 bp to 81 bp, 137 bp to 116 bp or 143 bp to 114 bp area integral is formed.

EXAMPLE 1 (DIAGNOSTIC QUERY)

a) Initial Clinical Situation

The patient to be investigated had mastopathy with suspected breast carcinoma. A blood sample was taken.

b) Query

Were there any circulating cancer cells able to form metastases in the blood sample taken?

c) Investigations and Results

| Investigation | Result |
| --- | --- |
| p53 mutation in tumour cells | NEGATIVE |
| p53 (exon5) mutation | NEGATIVE |
| p53 (exon6) mutation | NEGATIVE |
| p53 (exon7) mutations | NEGATIVE |
| p53 (exon8) mutations | NEGATIVE |
| erb-B2 after tumour cell isolation | POSITIVE |
| c-myc after tumour cell isolation | POSITIVE |
| CK20 mRNA | POSITIVE |
| CEA mRNA | POSITIVE |
| MUC1 mRNA | 0.95 |
| MUC1 mRNA fraction C | 1.40 |
| bFGF mRNA | NEGATIVE |
| bFGF-R mRNA | POSITIVE |
| VEGF mRNA | POSITIVE |
| VEGF-R1 mRNA | POSITIVE |
| VEGF-R2 mRNA | NEGATIVE |
| TIMP3 mRNA | NEGATIVE |
| MMP2 mRNA | NEGATIVE |
| Progesterone R mRNA | POSITIVE |
| Maspin mRNA | POSITIVE |
| Perforin after tumour cell isolation | NEGATIVE | d) Assessment

Cells which may be of the carcinoma type were detectable in the patient's blood circulation. Cancer cell-specific detection showed cells with enhanced transcription of the cancer-specific splice variant of the mucin1 gene. These cells also expressed CEA and CK20 mRNA. Since these expression characteristics are found in cases of breast carcinoma, the cells very probably originated from the breast, which was confirmed by the expression of maspin. The tumour cells could be concentrated in fraction C (MUC1) without lymphocytic contamination (perforin-negative). The detected cells also showed signs of an ability to metastasize because they expressed the bFGF and VEGF receptors, as well as VEGF, all of which are prerequisites for neoangiogenesis. The cells which have strayed into the blood expressed the progesterone receptor. The c-myc and erb-B2 amplification moreover indicated a poor prognosis. Qualitatively, this was a typical high-risk course with a huge potential for growth because these genes code for growth signals in the cancerous tissue.

e) Summary and Conclusion:

Overall, the findings indicated a spreading carcinoma with a poor prognosis based on the mastopathy.

EXAMPLE 2 (IDENTIFICATION OF THE SOURCE OF SPREAD)

a) Initial Clinical Situation

The patient to be investigated was suspected of having a colon or prostate carcinoma. A blood sample was taken.

b) Query

Were there any circulating cancer cells able to form metastases in the blood sample taken? Did these cells originate from a prostate or colon carcinoma?

c) Investigations and Results:

| Investigation | Result |
| --- | --- |
| K-ras after tumour cell isolation | POSITIVE |
| K-ras (exon1) mutation | POSITIVE |
| K-ras (exon1) mutation | NEGATIVE |
| CK20 mRNA | POSITIVE |
| CEA mRNA | NEGATIVE |
| MUC1 mRNA | >1.00 |
| Gastrin mRNA | POSITIVE |
| PSM mRNA | NEGATIVE |
| bFGF mRNA | NEGATIVE |
| bFGF-R mRNA | POSITIVE |
| VEGF mRNA | NEGATIVE |
| VEGF-R1 mRNA | NEGATIVE |
| VEGF-R2 mRNA | NEGATIVE |
| EGP mRNA | 255370 (corresponds to 100%) |
| GAPDH mRNA | 125836424 (corresponds to 100%) |
| EGP mRNA fraction C | 1773 (corresponds to 0.7% of fraction A) |
| GAPDH mRNA fraction C | 625 (corresponds to 0.0005% of fraction A) | d) Assessment

Cells spreading in the blood and transcribing exclusively the tumour-specific splice variant of the MUC1 gene as well as CK20, which are therefore to be assigned to the carcinoma type, were detectable. They could be concentrated in fraction C. The cells spreading in the blood certainly originated from the colon because gastrin mRNA was detectable, in contrast to prostate-specific PSM mRNA.

The point-mutated oncogene k-ras which is typical of colon carcinomas was also found in the epithelial cell fraction C. The detected cells likewise showed signs of an ability to metastasize because they expressed the bFGF receptor, a prerequisite for neoangiogenesis.

e) Summary and Conclusion:

Overall, the findings indicated a spreading carcinoma certainly to be found in the colorectal region. Therapy with Panorex appeared to be indicated because the cells expressed the EGP gene which is the therapeutic target.

EXAMPLE 3 (PROGNOSIS)

a) Initial Clinical Situation

The patient to be investigated had a malignant melanoma in the postoperative state (Clark II-III).

A blood sample was taken.

b) Query

Were there any circulating cancer cells able to form metastases in the blood sample taken? Was it possible to make any other prognostic statements about the tumour?

c) Investigations and Results:

| Investigation | Result |
| --- | --- |
| p53 mutation in tumour cells | POSITIVE |
| p53 (exon5) mutation | POSITIVE |
| p53 (exon6) mutation | NEGATIVE |
| p53 (exon7) mutations | NEGATIVE |
| p53 (exon8) mutations | NEGATIVE |
| Tyrosinase mRNA | POSITIVE |
| MAGE3 mRNA | POSITIVE |

-continued

| Investigation | Result |
| --- | --- |
| Muc18 mRNA | POSITIVE |
| bFGF mRNA | NEGATIVE |
| bFGF-R mRNA | POSITIVE |
| VEGF mRNA | POSITIVE |
| VEGF-R1 mRNA | POSITIVE |
| VEGF-R2 mRNA | NEGATIVE |
| MMP2 mRNA | POSITIVE |
| FAS mRNA in fraction C | POSITIVE |
| FAS receptor mRNA in fraction C | NEGATIVE |
| Perforin after tumour cell isolation | NEGATIVE | d) Assessment

The results indicated a progressive malignant melanoma with cells spreading in the blood and capable of metastasizing. The ability of the cells circulating in the blood to metastasize was indicated by the expression of the angiogenesis factors bFGF receptor, VEGF receptor 1 and VEGF, as well as the ability of the circulating cells to degrade matrix (detection of MMP2 mRNA).

A protein-relevant mutation of the oncogene p53 was found in Exon 5 in fraction C. The cells expressed only the FAS ligand but not the FAS receptor; they were possibly not accessible to cell-mediated cytotoxicity (apoptosis). Lymphocytic contamination of fraction C was ruled out because perforin was undetectable.

EXAMPLE 4 (RELEVANCE TO THERAPY)

a) Initial Clinical Situation

The patient to be investigated had a diagnosis of breast carcinoma (pT1b N1 M0). A blood sample was taken.

b) Query

Were there any circulating cancer cells able to form metastases in the blood sample taken? Was there any drug resistance?

c) Investigations and Results:

| Investigation | Result |
| --- | --- |
| p53 mutation in tumour cells | POSITIVE |
| p53 (exon5) mutation | NEGATIVE |
| p53 (exon6) mutation | NEGATIVE |
| p53 (exon7) mutations | NEGATIVE |
| p53 (exon8) mutations | POSITIVE |
| CK20 mRNA | POSITIVE |
| CEA mRNA | POSITIVE |
| MUC1 mRNA | 0.90 |
| MUC1 mRNA fraction C | 1.40 |
| bFGF mRNA | NEGATIVE |
| bFGF-R mRNA | POSITIVE |
| VEGF mRNA | POSITIVE |
| VEGF-R1 mRNA | POSITIVE |
| VEGF-R2 mRNA | NEGATIVE |
| Maspin mRNA | POSITIVE |
| MDR1 efflux doxorubicin test | 55% (Ref.: 40–65%) |
| MDR1 pump gp170 | 61% (Ref.: 40–65%) |
| MDR1 (human genome) | NEGATIVE |
| MDR mRNA fraction C | NEGATIVE |
| MRP mRNA fraction C | NEGATIVE |
| GST pi mRNA fraction C | NEGATIVE |
| Topoisomerase II mRNA fraction C | POSITIVE | d) Assessment

Cells which may be of the carcinoma type were detectable in the patient's blood circulation. Cancer cell-specific detection showed cells with enhanced transcription of the cancer-specific splice variant of the mucin1 gene. These cells also expressed CEA and CK20 mRNA. Since these expression characteristics are found in cases of breast carcinoma, the cells very probably originated from the breast, which was confirmed by the expression of maspin. The detected cells also showed signs of an ability to metastasize because they expressed the bFGF and VEGF receptors, as well as VEGF, all of which are prerequisites for neoangiogenesis. A p53 mutation in Exon 8 was also detectable in the tumour cell fraction. This is likewise a finding typical of breast carcinoma.

e) Summary and Conclusion:

Overall, the findings indicated a carcinoma capable of metastasis. There was no evidence of drug resistance in the patient. On the basis of the detected expression of topoisomerase as target gene, anthracycline therapy appeared to be indicated.

EXAMPLE 5 (BEFORE CHEMOTHERAPY)

a) Initial Clinical Situation

The patient to be investigated had a diagnosis of breast carcinoma. The patient was not receiving chemotherapy. A blood sample was taken.

b) Query

Were there any circulating cancer cells able to form metastases in the blood sample taken? Was there any drug resistance?

c) Investigations and Results:

| Investigation | Result |
| --- | --- |
| p53 mutation in tumour cells | NEGATIVE |
| p53 (exon5) mutations | NEGATIVE |
| p53 (exon6) mutation | NEGATIVE |
| p53 (exon7) mutations | NEGATIVE |
| p53 (exon8) mutations | NEGATIVE |
| erb-B2 after tumour cell isolation | NEGATIVE |
| c-myc after tumour cell isolation | NEGATIVE |
| CK20 mRNA | POSITIVE |
| CEA mRNA | POSITIVE |
| MUC1 mRNA | 0.55 |
| bFGF mRNA | NEGATIVE |
| bFGF-R mRNA | NEGATIVE |
| VEGF mRNA | NEGATIVE |
| VEGF-R1 mRNA | NEGATIVE |
| VEGF-R2 mRNA | NEGATIVE |
| MDR1 pump gp170 | 18%[1] (Ref.: 40–65%) |
| MDR1 (human genome) | NEGATIVE |
| MDR1 mRNA | POSITIVE |
| GST pi mRNA | POSITIVE |
| Topoisomerase II mRNA | POSITIVE |
| MRP mRNA | POSITIVE |
| EGP mRNA | 30743 (corresponds to 100%) |
| GAPDH mRNA | 1765600 (corresponds to 100%) |
| EGP mRNA fraction C | 1 |
| GAPDH mRNA fraction C | 0 |
| MUC1 mRNA fraction C | >1.00 |
| bFGF mRNA fraction C | 0.00 |

[1]Nonspecific antibody-binding capacity (ABC): 953 Specific ABC: 2935 e) Assessment

Cells of the carcinoma type which transcribed the cancer-specific splice variant of the MUC1 gene were detectable in the patient's blood circulation. Expression of CEA and CK20 was also detectable. These expression characteristics indicated a breast carcinoma. Since analysis of the above angiogenesis factors had negative results, it was possible to assume that the circulating cancer cells showed only a low potential for metastasis. There was no evidence of drug resistance in the patient.

e) Summary and Conclusion:

Overall, the findings indicated a spreading breast carcinoma without signs of drug resistance.

EXAMPLE 6 (AFTER CHEMOTHERAPY)

a) Initial Clinical Situation

The patient was the same one as described in Example 5. On the basis of the findings in Example 5, the patient was treated with an adjuvant chemotherapy and with tamoxifen. Blood was again taken from the patient after completion of the chemotherapy.

b) Query

Were there any circulating cancer cells able to form metastases in the blood sample taken?

c) Investigations and Results:

| Investigation | Result |
| --- | --- |
| anti-p53 | low |
| Pan p53 | 243 pg/ml |
|  | normal up to 646 |
|  | marginal up to 786 |
|  | pathological above 787 |
| c-erb-B2 | 2610 HNU/ml |
|  | normal up to 3385 |
|  | marginal 3386–3845 |
|  | pathological >3845 |
| p53 mutation in tumour cells | NEGATIVE |
| p53 (exon5) mutation | NEGATIVE |
| p53 (exon6) mutation | NEGATIVE |
| p53 (exon7) mutations | NEGATIVE |
| p53 (exon8) mutations | NEGATIVE |
| erb-B2 after tumour cell isolation | NEGATIVE |
| c-myc after tumour cell isolation | NEGATIVE |
| CK20 mRNA | NEGATIVE |
| CEA mRNA | NEGATIVE |
| MUC1 mRNA | 0.60 |
| bFGF mRNA | NEGATIVE |
| bFGF-R mRNA | POSITIVE |
| VEGF mRNA | weak positive |
| VEGF-R1 mRNA | POSITIVE |
| VEGF-R2 mRNA | NEGATIVE |
| TIMP3 mRNA | NEGATIVE |
| MMP2 mRNA | NEGATIVE |
| Progesterone R mRNA | POSITIVE |
| EGP mRNA | 232255 (corresponds to 100%) |
| GAPDH mRNA | 463040096 (corresponds to 100%) |
| EGP mRNA fraction C | 0 |
| GAPDH mRNA fraction C | 203 (corresponds to 0.00004% of fraction A) |
| MUC1 mRNA fraction C | 0.00 | d) Assessment

Cells which may be of the carcinoma type were detectable in the patient's blood circulation. Cancer cell-specific detection showed cells with enhanced transcription of the cancer-specific splice variant of the mucin1 gene. The detected cells showed first signs of an ability to metastasize; they expressed bFGF-R, VEGF and VEGF-R1 mRNA; however MMP-2 was undetectable. The cells which had strayed into the blood were progesterone receptor-positive.

Of the prognostic oncoproteins, anti-p53 was detectable; this reactive protein due to p53 mutations indicated a worse prognosis.

e) Summary and Conclusion:

Overall, the findings indicated a carcinoma still spreading. However, the picture showed a distinct change from the previous findings (before chemotherapy). Thus, in particular, MUC1 was no longer detectable in fraction C, and the markers CK20 and CEA were negative in fraction A. This indicated a distinct success of the therapy.

EXAMPLE 7 a) Initial Clinical Situation

The patient to be investigated was suspected of having an ovarian carcinoma. A blood sample was taken.

b) Query

Were there any circulating cancer cells able to form metastases in the blood sample taken? Was there any drug resistance?

c) Investigations and Results

| Investigation | Result |
| --- | --- |
| anti-p53 | NEGATIVE |
| Pan p53 | 440 pg/ml |
|  | normal up to 646 |
|  | marginal up to 786 |
|  | pathological above 787 |
| c-erb-B2 | 2641 HNU/ml |
|  | normal up to 3385 |
|  | marginal 3386–3845 |
|  | pathological >3845 |
| p53 mutation in tumour cells | NEGATIVE |
| p53 (exon5) mutation | NEGATIVE |
| p53 (exon6) mutation | NEGATIVE |
| p53 (exon7) mutations | NEGATIVE |
| p53 (exon8) mutations | NEGATIVE |
| erb-B2 after tumour cell isolation | NEGATIVE |
| c-myc after tumour cell isolation | NEGATIVE |
| CK20 mRNA | NEGATIVE |
| CEA mRNA | NEGATIVE |
| MUC1 mRNA | 0.35 |
| bFGF mRNA | NEGATIVE |
| bFGF-R mRNA | NEGATIVE |
| VEGF mRNA | not assessable |
| VEGF-R1 mRNA | NEGATIVE |
| VEGF-R2 mRNA | NEGATIVE |
| Progesterone R mRNA | weak positive |
| MDR1 mRNA | POSITIVE |
| Topoisomerase II mRNA | NEGATIVE |
| MDR1 efflux doxorubicin test[1] | 0% |
| MDR1 pump gp170[2] | 0% |
| Glutathione S-transferase mRNA | POSITIVE |
| MRP mRNA | POSITIVE |

[1]Note on the parameter:
In contrast to the control cells, the lymphocytes were unable to accumulate any doxorubicin. This made determination of the efflux impossible.
[2]Note on the parameter:

| Investigation | Result |
|---|---|
| Compared with the positive control cells, no expression of the MDR1 pump gp710 was detectable on the lymphocytes. Quantitative analysis revealed the following: Nonspecific antibody binding capacity (ABC): 1523 Specific ABC: 4165 | | d) Assessment

Cancer cells of the carcinoma type with enhanced transcription of the cancer-specific splice variant of the MUC1 gene were detectable in the patient's blood circulation.

Since analyses of the above angiogenesis factors had negative results, it was not possible to detect any cells capable of neoangiogenesis, the functional interplay of endothelial and epithelial cells. The circulating cancer cells therefore showed no ability to metastasize; there was not assumed to be any formation of active metastases. The cells circulating in the blood expressed the progesterone receptor. There was no evidence of drug resistance in the patient.

e) Summary and Conclusion

Overall, the findings possibly indicated a carcinoma of a hormone-sensitive organ.

EXAMPLE 8 a) Initial Clinical Situation

The patient to be investigated had a suspect breast finding (walnut-sized tumour with unremarkable mammography) leading to suspicion of breast carcinoma. In the family there were known to be three cases of breast neoplasms, including two in patients less than 50 years of age, and one case of an ovarian neoplasm. Hence there was a genetic predisposition to tumours. A blood sample was taken.

b) Query

Were there any circulating cancer cells able to form metastases in the blood sample taken?

c) Investigations and Results

| Investigation | Result |
|---|---|
| anti-p53 | NEGATIVE |
| Pan p53 | 87 pg/ml normal up to 646 marginal up to 786 pathological above 787 |
| c-erb-B2 | 2540 HNU/ml normal up to 3385 marginal 3386–3845 pathological >3845 |
| p53 mutation in tumour cells | NEGATIVE |
| p53 (exon5) mutation | NEGATIVE |
| p53 (exon6) mutation | NEGATIVE |
| p53 (exon7) mutations | NEGATIVE |
| p53 (exon8) mutations | NEGATIVE |
| erb-B2 after tumour cell isolation | NEGATIVE |
| c-myc after tumour cell isolation | NEGATIVE |
| CK20 mRNA fraction A | POSITIVE |
| CEA mRNA fraction A | weak positive |
| MUC1 mRNA fraction A | 0.86 |
| bFGF mRNA fraction A | POSITIVE 909 corresponds to 100% (fraction A) |
| bFGF-R mRNA fraction A | NEGATIVE |
| VEGF mRNA fraction A | POSITIVE 72437 corresponds to 100% (fraction A) |
| VEGF-R1 mRNA fraction A | NEGATIVE |
| VEGF-R2 mRNA fraction A | NEGATIVE |
| TIMP3 mRNA fraction A | POSITIVE |
| MMP2 mRNA fraction A | weak positive |
| Progesterone R mRNA | NEGATIVE |
| EGP mRNA fraction A | 104097 (corresponds to 100%) |
| GAPDH mRNA fraction A | 153350963 (corresponds to 100%) |
| CK20 mRNA fraction C | NEGATIVE |
| CEA mRNA fraction C | NEGATIVE |
| MUC1 mRNA fraction C | 0.00 |
| bFGF mRNA fraction C | 0.00 |
| VEGF mRNA fraction C | 1738 (2.4% based on fraction A) |
| TIMP3 mRNA fraction C | NEGATIVE |
| MMP2 mRNA fraction C | NEGATIVE |
| EGP mRNA fraction C | 0 |
| GAPDH mRNA fraction C | 108644 (corresponds to 0.00708% of fraction A) | d) Assessment

Small amounts of cancer cells of the carcinoma type with enhanced transcription of the cancer-specific splice variant of the MUC1 gene were detectable in the patient's blood circulation. Expression of CK20 and CEA was also detectable. These expression characteristics indicated a breast carcinoma. However, it was not possible to concentrate the circulating cancer cells. Since the analyses of the above angiogenesis factors had positive results in some instances (expression of bFGF and VEGF), cells capable of neoangiogenesis, the functional interplay of endothelial and epithelial cells, were detectable. The circulating cancer cells therefore showed signs of an ability to metastasize. This was also indicated by the expression of the MMP2 gene. The formation of active metastases was therefore very probable. The progesterone receptor was not expressed by the cells in the blood circulation.

e) Summary and Conclusion

Overall, the findings indicated a spreading carcinoma. The circulating cells originated from the breast.

GLOSSARY

AFP (Alpha-Fetoprotein)

AFP is the main plasma protein in the fetus. There is very little expression of AFP in adults unless a tumour such as a hepatoma or a teratoma is present.

Ref.: Gibbs et al.; Biochemistry 26: 1332–1343, 1987.

B-Actin

Ref.: Pollard, T. D. and Cooper, J. A.; Ann. Rev. Biochem. 55, 987 ff, 1986.

Albumin (ALB)

Albumin is used for identifying hepatoma cells circulating in the blood.

Ref.: Minghetti et al.; J. Biol. Chem. 261: 6747–6757, 1986.

AR (Androgen Receptor)

Synonyms: Dihydrotestosterone receptor, testosterone receptor, TFM

Prostate carcinoma cells are dependent on the growth-stimulating effect of the AR. In prostate carcinomas it has been possible to detect mutations in the androgen receptor, some of which lead to a receptor with constitutive activity.
Ref.: Lubahn et al.; Proc. Natl. Acad. Sci. USA 87(11): 9534–9538, 1989.

BA46 (Breast Epithelial Antigen 46)

Synonym: human milk fat globule protein

The glycoprotein BA-46 is expressed by breast carcinomas and has been used successfully as the target of experimental radioimmunotherapies.
Ref.: Couto et al.; DNA Cell Biol. 15: 281–286, 1996.

Basic Fibroblast Growth Factor (bFGF)

Synonym: FGF-2

There is overexpression of bFGF in many types of tumours and it can therefore be regarded as a factor for the ability to metastasize.
Ref.: Abraham et al.; EMBO J. 5: 2523–2528, 1986.

BAX

The bcl-2 product heterodimerizes in vivo with a conserved homologue, BAX, which expedites programmed cell death.
Ref.: Tsujimoto Y. and Croce C. M.; PNAS, 83 (14), 5214–5218, 1986.

bcl-2

The bcl-2 gene was discovered in follicular non-Hodgkin lymphomas (B-cell lymphomas). BCL-2 can block apoptosis.
Ref.: Tsujimoto Y. and Croce C. M.; PNAS, 83 (14), 5214–5218, 1986.

BRCA1

The BRCA1 gene is a tumour suppressor gene. 5–10% of patients with breast cancer have a genetic predisposition, which is frequently associated with a predisposition for ovarian carcinomas too. Mutations in the BRCA1 gene are associated with 45% of breast carcinomas with a genetic component. Mutations in the BRCA1 gene also relate to ovarian carcinomas.
Ref.: Smith T. M., et al.; Genome Res. 6, 1029–1049, 1996.

BRCA2

The BRCA2 gene is a tumour suppressor gene. Mutations in this gene are thought to be responsible for a large proportion of hereditary breast tumours which develop early.
Ref.: Lancaster J. M., et al.; Nature Genet. 13, 238–240, 1996.

Calcitonin

Calcitonin (32 amino acids) is, like calcitonin gene-related peptide (CGRP; 37 amino acids), encoded by the calc-1 gene. Calcitonin can inhibit the growth of a gastric carcinoma cell line, and the neurohormone CGRP can act as autocrine growth factor for murine carcinoma cell lines.
Ref.: Adema and Baas; BBRC 178: 985–992, 1991.

CC10 (Clara Cell 10 kD Protein)

CC10 is expressed only in type 2 alveolar epithelial cells and in Clara cells of the pulmonary epithelium and is involved in the production of epithelial lining fluid.
Ref.: Hay J. G. et al, Am. J. Physiol. 268: L565 (1995).

CCK (Cholecystokinin)

CCK is a brain and bowel hormone. CCK is additionally expressed by some sarcoma/neuroepithelioma cell lines.
Ref.: Friedman, J. M. et al.; PNAS 89: 5819–5823, 1992.

CD44

Synonyms: Hermes antigen, Pgp-1

The CD44 glycoprotein is a cell adhesion molecule. Certain splice variants of CD44 are involved in the process of tumour metastasis.
Ref.: Matsumura, Y. and Tarin, D.; The Lancet 340, 1053–1058, 1992.

CEA (Carcinoembryonic Antigen)

Synonym: CD66e

CEA is expressed in gastrointestinal and colorectal carcinomas, but also in various solid tumours such as breast carcinomas, in the foetal colon, but not in normal lymphocytes. Because of this expression profile, detection of CEA-positive cells in the blood is used for diagnosing circulating tumour cells. In addition, CEA immunoassays are important diagnostic methods for the observation of cancer patients, especially in cases of colon carcinoma.
Ref.: Zimmermann et al.; Proc. Natl. Acad. Sci. USA 84: 2960–2964, 1987.

CK20 (Cytokeratin 20)

Malignant cells usually retain the cytokeratin pattern, and this can accordingly be used for localizing the tumour cells back to an epithelium. Since CK20 is not expressed by peripheral blood cells but mainly by cells of the gastrointestinal tract, this cytokeratin is used for detecting tumour cells originating therefrom and circulating in the blood.
Ref.: Moll et al.; Differentiation 63: 75–93, 1993; Burchill et al.; British Journal of Cancer 71:278–281, 1995.

Cyclin A, B(1), D1, D2, D3, and E

Cyclins and cyclin-dependent kinases (CDK) are essential for control of the cell cycle of eukaryotic cells. Measurement of the cyclins correlates with the cell cycle.
Ref.: Motokura T., et al.; J. Biol. Chem. 1992 Oct. 5; 267(28): 20412–5;
Lees E., et al.; Genes-Dev. 1992 October; 6(10): 1874–85.

Cyclin G

Cyclin G1 and cyclin G2 are two only recently identified cyclins which play a part in the cell cycle.
Ref.: Horne M. C., et al.; J. Biol. Chem. 1996 Mar. 15; 271(11): 6050–61.

DCC

Sequences are frequently deleted from chromosome 18 in colorectal tumours (DCC=deleted in colorectal carcinomas). Expression of the DCC gene is greatly reduced in most colorectal carcinomas. Loss of the 18q region is associated with a poor prognosis. The status of the DCC gene can be determined by means of microsatellite markers and PCR on formalin-fixed material.

Ref.: Frank C. J., et al.; Cancer Res. 57, (5), 824–827, 1997.

DPC4

The name means "deleted in pancreatic carcinoma". About 90% of human pancreatic carcinomas show an allele loss on chromosome 18. A tumour suppressor gene is involved. Changes in the DPC4 gene have also been discovered in breast and ovarian carcinomas.
Ref.: Hahn S. A., et al.; Science 271, 350–354, 1996.

E-Cadherin

Catenin (α- and β-)

E-Cadherin is important, in conjunction with associated catenins (α-catenin; β-catenin), for organogenesis and histogenesis of epithelial tissue and plays a central part in the process of carcinoma metastasis.
Ref.: Aberle H., et al.; J. Cell. Biochem. 1996 Jun. 15; 61(4): 514–23.

EGF (Epidermal Growth Factor)

Synonyms: HMGF (human milk growth factor); PGF (prostatic growth factor); urogastrone EGF is involved in embryonic development (ectodermal, mesodermal and endodermal cells) and controls/stimulates the proliferation of epidermal and epithelial cells in vitro. EGF may likewise act as an angiogenic and chemotactic factor.
Ref.: Carpenter: EGF; Curr. Opin. Cell. Biol. 5: 261–264, 1993.

EGF-R (EGF Receptor)

Synonym: SA-7 (species antigen 7)

There is overexpression of EGF-R in some human tumours, and this correlates with the aggressiveness of the tumour; a poor prognosis is indicated by coexpression of EGF-R with either c-erb-B2 or TGF-alpha.
Ref.: Ibelgaufts: Dictionary of cytokines, VCH, 1994.

EGP (Epithelial Glycoprotein)

Synonyms: GA733-2; 17-1A antigen; KS1/4

Epithelial glycoprotein can be used as epithelium-specific marker for detecting carcinomas.
Ref.: Simon, B. et al.; PNAS 87: 2755–2759, 1990; Szala, S. et al.; PNAS 87: 3542–3546, 1990.

Enteroglucagon

Synonyms: EG, glucagon 37

Enteroglucagon is a peptide produced by jejunoileal cells.
Ref.: Bell, G. I. et al.; Nature 304: 368–371, 1983.

erb-B

The erb-B gene codes for the receptor (EGF-R) of epidermal growth factor (EGF). This gene is amplified in about 50% of advanced human glioblastomas.
Ref.: Haley J., et al.; Oncogene Res. 1, 375–396, 1987.

erb-B2

Synonyms: c-erb-B2; avian erythroblastic leukaemia viral oncogene homologue 2; NGL (neuroblastoma or glioblastoma-derived); neu; tyrosine kinase-type cell surface receptor HER2; TKR1

Erb-B2 encodes a tumour antigen, P185, which is serologically related to the epidermal growth factor receptor (EGF-R). Overexpression converts the gene for a normal growth factor receptor, erb-B2, into an oncogene. Amplification of erb-B2 is observed in adenocarcinomas and in breast and ovarian cancer. Erb-B2 is additionally involved in the development of acute promyelocytic leukaemia (APL) because the gene is located in band q21.1 of chromosome 17 where the breakpoint of the translocation between chromosome 15 and 17 is also located (t15:17).
Ref.: Slamon et al.; Science 244: 707–712, 1989.

FAP (APC)

The gene of familial adenomatous polyposis coli, an autosomal dominant disorder, is fap.
Ref.: Groden J. et al.; Cell 66: 589–0, 1991.

FAS-R; FAS-L (CD95, CD95-L)

FAS belongs to the group of apoptosis-inducing factors.
Ref.: Alderson M. R.; J. Exp. Med. 181, (1), 71–77, 1995; Itoh N.; Cell 66, (6), 233–243, 1991.

FGF Receptors

Synonyms: fms-like tyrosine kinase-2; FLT2; FMS-like gene; FLG (bFGF-R1); K-SAM, bek (FGF-R2)

Differences in expression and alternative splicing may be critical in the malignant progression of tumours.
Ref.: Yamaguchi et al.; Proc. Natl. Acad. Sci. USA 91: 484–488, 1994.

c-fos

The c-fos and c-jun genes play a central part in growth regulation.
Ref.: Ekstrand A. J., et al.; Exp. Cell. Res. 169. 262–266, 1987.

GADD45

Gadd45 is a growth arrest- and DNA damage-induced gene which is regulated by the p53 tumour suppressor gene.
Ref.: Constance, C. M. et al.; Mol. Cell. Biol. 1996 July; 16 (7): 3878–83
Crawford, D. R. et al.; Arch. Biochem. Biophys. 1996 May 15; 329(2): 137–44.

GAPDH (glyceraldehyde-3-phosphate dehydrogenase)

This gene is expressed in all cells. Expression of this gene correlates with the number of cells and is used for quantitative and qualitative determination of cDNA.
Ref.: Allen, R. W. et al.; J. Biol. Chem. 262 (2), 649–653, 1987.

Gastrin (GAS)

Gastrin is produced mainly by mucosal cells of the stomach and the D cells in the pancreas.
Ref.: Boel, E. et al.; PNAS 80: 2866–2869, 1983.

GD-AIF (Glioma-Derived Angiogenesis Inhibitory Factor)

GD-AIF is, just like thrombospondin and angiostatin, one of the endogenous negative regulators of angiogenesis. The extent to which the negative regulators decrease during the changeover phase to the angiogenic phenotype of tumour genesis decides whether a primary tumour grows slowly or quickly and whether metastases are formed.
Ref.: Folkman J.; Nat. Med. 1 (1995) 27–31.

GIP (Gastric Inhibitory Polypeptide)

Synonym: glucose-dependent insulinotropic polypeptide

This hormone is mainly produced by cells in the upper small intestine.

Ref.: Inagaki, N. et al.; Molec. Endocr. 3: 1014–1021, 1989.

GST-pi (glutathione S-transferase pi)

GST-pi codes for a detoxifying enzyme and is therefore involved in the development of drug-resistant tumours. An increase in expression has been observed in tumours after chemotherapy, which is associated with an unfavourable prognosis and drug resistance.
Ref.: Morrow et al.; Gene 75: 3–11, 1989.

Granzyme

The main function of the granzymes is to lyse tumour cells and virus-infected cells by apoptotic fragmentation of the DNA.
Ref.: Kummer, J. A. et al.; Kidney Int. 47: 70–77 (1995).

hCG (Human Chorionic Gonadotropin)

The β subunit of hCG is used as marker for germ line tumours and choriocarcinomas, and detection of hCG mRNA by RT-PCR is also useful in the diagnosis of metastasizing breast carcinomas and malignant melanomas.
Ref.: Doi F. et al; Int. J. Cancer 65 (1996) 454–459.

HIC-1 (Hypermethylated in Cancer)

HIC-1 is regarded as a possible tumour suppressor gene product. Underexpression takes place in tumour cells in which it is hypermethylated.
Ref.: Wales M. M., et al.; Nat. Med. 1 (1995) 570–577.

HSP70

Heat shock proteins such as HSP70 may play a part in escape mechanisms of tumour cells.
Ref.: Kaur J. and Ralhan R.; 63(6): 774–9.

hTG (Human Thyroglobulin)

hTG is a thyroid protein. Four transcripts resulting from alternative splicing have been identified.
Ref.: Bertaux et al.; Gene 156: 297–301, 1995.

ICAM (Intercellular Adhesion Molecules)

Synonyms: ICAM-1 (CD54, ICAM1-1); ICAM-2 (CD102); ICAM-3 ICAM-1, -2, and -3 are cell surface molecules which act as ligands of leukocyte integrins.

IGF (Insulin-Like Growth Factor)

Synonyms: MSA (multiplication-stimulating activity); somatomedin; NSILA (non-suppressible insulin-like activity); SF (sulphation factor), SFA, SGF (skeletal growth factor), SMP IGFs act as mitogenic, autocrine and angiogenic factors.
Ref.: Cohick and Clemmons; Annual Review of Physiology 55: 131–153, 1993.

IGF-BP3 (Insulin-Like Growth Factor Binding Protein 3)

Synonyms: IGBP; IBP; BP-53; growth hormone dependent binding protein; binding protein 29

IGF-BP3 acts as growth inhibitor.
Ref.: Lamson; Growth factors 5: 19–28, 1991.

Integrins

Integrins are heterodimeric cell surface antigens which are involved in cell—cell and cell-matrix interactions.
Ref.: VIth International Human Leukocyte Differentiation Antigen Workshop and Conference, Kobe (Japan), November 1996.

Interferon-Gamma

Synonyms: immune interferon; type 2 interferon; T interferon; antigen-induced interferon; mitogen-induced interferon; ph2-labile interferon
Ref.: Gray et al.; Nature 295: 503–508, 1982;
Ibelgaufts: Dictionary of cytokines. VCH 1994.

LOHs

Inactivation of tumour suppressor genes is a critical step in the development of tumours. Common mechanisms are both inactivating mutations and the genomic loss of the entire gene or of parts of the gene. The genomic loss of chromosome sections can be envisaged experimentally by the loss of heterozygosity (=LOH). Both alleles of the tumour suppressor gene are found in a patient's normal tissue, whereas only one allele is detectable in the tumour. The two alleles are identified by means of highly polymorphic chromosomal regions located inside or in the vicinity of the tumour suppressor gene (microsatellite repeats), which are amplified by a PCR. These are repeats of short nucleotide sequences (for example CA repeats, CGG repeats), but there are differences in the copy number and thus the product amplified in the PCR varies in length.

L32

The ubiquitous expression of L32 makes it suitable as target gene for quantification.
Ref.: Young, J. A. and Trowsdale, J.; Nucleic Acids Res. 13 (24), 8883–8891, 1985.

LRP

Synonyms: protein tyrosine phosphatase; alpha-polypeptide; PTPRA; PTPA

Lrp codes for a ubiquitously expressed protein tyrosine kinase.
Ref.: Jirik et al.; FEBS Lett. 273: 239–242, 1990.

MAGE1 (Melanoma Associated Antigen-1)

Synonym: MZ2-E

The MAGE1 gene codes for an antigen on the surface of melanoma cells. Whereas MAGE1 can be detected at a high level in many tumours at the RNA level, the RNA is not found in normal tissues with the exception of testis and ovary. This gene product is thus extremely suitable as marker for circulating tumour cells, in particular melanoma cells.
Ref.: De Plaen et al.; Immunogenetics 40: 360–369, 1994.

MAGE3 (Melanoma Associated Antigen-3)

The MAGE3-encoding gene is transcribed in about 69% of melanomas. Since it has hitherto been found only in tumour tissue and in no normal tissue apart from testis, this gene is suitable as marker for circulating melanoma cells.
Ref.: Gaugler et al.; J. Exp. Med. 179: 921–930, 1994.

Maspin

Maspin is a tumour suppressor gene. Defects in this gene are found in particular in breast carcinoma cells.
Ref.: Luppi et al.; Annals of Oncol. 7: 619–624, 1996.

mdm2

The oncogenic effect of increased MDM2 activity is made evident by inactivation of the p53-induced growth inhibition. Consistent with this, overexpression of mdm2 is found in human tumours.

Ref.: Zaubermann et al.; Nucleic Acids Res. 23: 2584–2592, 1995.

β2-Microglobulin

β2-microglobulin is expressed on all nucleated vertebrate cells.
Ref.: Williams, A. F. and Barclay, A. N.; Annu. Rev. Immunol. 6, 381; 1988.

MLH1

Synonyms: FCC2; COCA2; HNPCC (hereditary nonpolyposis colorectal cancer type 2)

MLH1 gene mutations are responsible for about 30% of a hereditary form of colon carcinoma (hereditary nonpolyposis colon cancer=HNPCC). About 60% of HNPCC cases are, however, caused by mutations in the MSH2 gene on chromosome 2. Two other human genes homologous with MutL have been isolated: pms-1 and pms-2. However, these are less commonly involved than msh2 and mlh1 in the development of tumours.
Ref.: Bellacosa et al.; Am. J. Med. Genet. 62: 353–364, 1996.

MMP (Metalloproteinase)

MMPs are $Zn^{2+}$-binding endopeptidases which degrade components of the extracellular matrix. They are involved in angiogenesis and tumour invasion. There are at least 11 MMPs. Overexpression of metalloproteinases promotes tumour invasion and metastasis. There is enhanced expression of some of these metalloproteinases by tumour cells both on the cell surface and at the mRNA level.
Ref.: Freije et al.; J. Biol. Chem. 269: 16766–16773, 1994; Sato et al.; Nature 370: 61–65, 1994.

Motilin (MIN)

Motilin is a hormone produced by cells of the small intestine.
Ref.: Daikh, D. I et al.; DNA 8: 615–621; 1989.

MRP1 (Multidrug Resistance-Associated Protein-1)

The MRP gene codes for a chemotherapeutic efflux pump which is located in the plasma membrane and has similarities with the ATP-binding cassette superfamily of transport systems, which also includes MDR1 and the cystic fibrosis transmembrane conductance regulator. Overexpression of MDR1 attributable to genomic amplification of the gene was detectable in a drug-resistant cell line of small-cell lung carcinoma.
Ref.: Cole et al.; Science 258: 1650–1654, 1992.

MSH2

This gene plays a part in tumours developed by patients with hereditary nonpolyposis colorectal cancer (HNPCC). MSH2 mutations have been found in 21% of families affected by HNPCC.
Ref.: Fishel R., et al.; Science 266, 1403–1405, 1994.

MUC1 (Mucin-1)

Synonyms: PUM, PEM

The MUC1 gene encodes a transmembrane glycoprotein which is formed by tumour cells to protect against cytotoxic immune cells and to promote metastasis. MUC1 is synthesized by normal tissues and cells but also by malignant cells and tissues. For example, breast cancer, pancreatic cancer and adenocarcinoma cells show overexpression of the MUC1 protein; moreover, a tumour-specific splice variant is detected in addition to the "normal" variant in some types of cancer.
Ref.: Weiss et al.; Int. J. Cancer 66: 55–59, 1996.

Muc18

Muc18 codes for a glycoprotein whose expression is restricted to advanced primary and metastasizing melanomas and to cell lines of the neuroectodermal line. In about 80% of melanomas there is found to be mRNA expression, and the expression correlates with the metastasis status of the cells. The presence of cells expressing this mRNA in the blood is good evidence of circulating tumour cells from an advanced or metastasizing melanoma.
Ref.: Lehmann et al.; Proc. Natl. Acad. Sci. USA 86:9891–9895, 1989.

myc

Synonyms: proto-oncogene homologous to myelocytoma virus; c-myc

Amplification of c-myc is found in advanced and in aggressive primary tumours.
Ref.: Adams et al.; Proc. Natl. Acad. Sci. 80: 1982–1986, 1983.

N-CoR

N-CoR is a corepressor protein for the retinoic acid β receptor.
Ref.: Soderstrom et al.; Mol. Endocrinol. 11:682 (1997).

Neurotensin (NTS)

Neurotensin is a small neuropeptide localized in the catecholamine-containing neurons.
Ref.: Bean, A. J. et al.; Neuroscience 50: 259–268, 1992.

NF-1

The NF1 gene is a tumour suppressor gene. The product of the neurofibromatosis-1 gene is neurofibromin or NF1-GAP. NF-1 mutations were found in 10 families with neurofibromatosis (von Recklinghausen's disease).
Ref.: Marchuk D. A., et al.; Genomics 11, 931–940, 1991.

NF-2

Synonym: merlin

Defects in the NF-2 tumour suppressor gene have been found in type II neurofibromatosis, a hereditary malignant disorder with bilateral tumours of the 8th cranial nerve, neurofibromas, meningiomas, gliomas or schwannomas and in sporadic meningiomas, schwannomas and, in addition, in melanomas and breast carcinomas.
Ref.: Trofatter et al.; Cell 72: 791–800, 1993.

nm23

The nm23-H1 gene is a potential metastasis suppressor. Expression is inversely proportional to the development of lymph node metastases.
Ref.: Royds J A., et al.; J. Natl. Cancer Inst. 85, 727–31, 1993.

ER (Oestrogen Receptor)

Apart from its function as an important regulator of the growth and differentiation of the mammary gland and the female reproductive tract, the oestrogen receptor is involved in the development of breast carcinomas. The content of oestrogen and progesterone receptor in a tumour is thus an important prognostic marker for the success of endocrine therapy. A number of splice variants of the oestrogen receptor have been described and attributed with a function in the development and metastasis of tumours. Thus, a variant of the oestrogen receptor lacking Exon 5 has been found inter alia in breast cancer cell lines and tumours.

Ref.: Greene et al.; Science 231: 1150–1154, 1986.

P-glycoprotein (MDR1)

Synonyms: PGY-1; MDR1; GP170 doxorubicin resistance gene; multidrug resistance gene The mdr1 gene codes for a cytostatic efflux pump located in the apical membrane. Treatment of tumours with chemotherapeutic agents often encounters multidrug resistance to a large number of structurally different therapeutic agents simultaneously. It has been observed experimentally that the mdr1 locus is amplified under the influence of chemotherapeutic agents. Increased expression of this gene has been found in drug-resistant cell lines.

Ref.: Gros et al.; Cell 47: 371–380, 1986.

p16

Synonyms: p16(INK4) or CDKN2; MTS1

P16 is the name given to cyclin-dependent kinase inhibitors. Deletions of mts1 are characteristic for a large number of tumours. Both deletions and mutations of this gene have been found in melanomas. The frequency of deletions of the CDKN2 gene in tumour cells indicates a tumour suppressor gene.

Ref.: Stone S., et al.; Cancer Res. 55, 2988–2994, 1995.

p21

P21 refers to the human cyclin-dependent kinase inhibitor.

Ref.: Harper J. W., et al.; Cell 75 (4), 805–16, 1993.

p53

Mutations in the p53 gene are among the commonest genetic alterations in malignant tumours in humans. In most of these tumours there is found to be loss of one allele of the p53 gene (breast carcinoma (32–64%); ovarian carcinoma (44–66%); gastric carcinoma (>60%); bladder carcinoma (38–58%); pancreatic carcinoma (70%); lung carcinoma (20%); prostate carcinoma (59%); cervical carcinoma (50%)). The mutations are distributed along the entire length of the protein, with clustering in Exons 5 to 8 and some other exons also frequently being affected (codons 175, 245, 248, 249, 273). The frequency of these hotspot mutations varies with the organ of origin of the tumour. Mutations in codon 175 are found, for example, in 6% of breast carcinomas, 14% of colorectal tumours and 4% of ovarian carcinomas. They are almost exclusively point mutations occurring over a wide region of the gene.

Ref.: Levine A. J.; Nature 351, 453, 1991.

PDGF (Platelet-Derived Growth Factor)

Synonyms: FDGF; GDGF; GDGF-1; GDGF-2; GSM; MDF; MDGF; ODGF; T47D factor

PDGF is a local autocrine and paracrine growth factor with chemotactic activity, a potent vasoconstrictor and angiogenesis factor.

Ref.: Westermark und Sorg: Biology of platelet-derived growth factor. Karger, Basel 1993.

Peptide YY

Synonym: PYY

There is endocrine synthesis of PYY by cells of the small intestine, the colon and the pancreas.

Ref.: Hort, Y. et al.; Genomics 26: 77–83, 1995.

Perforin-1

Synonyms: cytolysin; C9-related protein; pore-forming protein; PFP

Perforin-1 belongs to a class of cytolytic proteins which permeabilize the membranes of target cells.

Ref.: Ojcius und Young; TIBS 16: 225–229, 1991.

PR (Progesterone Receptor)

Synonym: PGR

A large content of progesterone receptor in a breast carcinoma is a prognostic marker for the response to endocrine therapy and prolonged survival. Consistent with this, progesterone has a protective effect in relation to breast cancer. Analysis of the progesterone receptor in breast carcinomas is of particular interest because the presence of the oestrogen receptor can also be determined indirectly.

Ref.: Misrahi et al.; Biochem. Biophys. Res. Commun. 143: 740–748, 1987.

PSM (Prostate-Specific Membrane Antigen)

Normal and neoplastic prostate cells express PSM.

Ref.: Israeli et al.; Cancer Res. 53: 227–230, 1993.

PSA (Prostate-Specific Antigen)

Synonym: APS

The PSA level is measured in radioimmunoassays for the diagnosis and monitoring of prostate carcinomas.

Ref.: Lundwall et al.; FEBS Lett. 214: 317–322, 1987.

Ras

The cellular genes of the ras gene family are named after the corresponding retroviral oncogenes. Their names are: c-Harvey-ras (c-H-ras), c-Kirsten-ras (c-K-ras) and N-ras (discovered in neuroblastomas).

Mutations in codons 12, 13 and 61 are found both in solid and in haemopoietic tumours. RAS mutations can frequently be detected in pancreatic, thyroid and colorectal carcinomas. Most of the mutations in colorectal tumours are G-A transitions, which permits conclusions to be drawn about alkylating agents.

Ref.: Bos J. L.; Cancer Res., 49, 4682–9, 1989.

RB (Retinoblastoma)

Loss or inactivation of the RB gene is crucial for the development of retinoblastomas. Loss of the function of the gene in both alleles leads to development of the tumour. Microsatellites and RFLP can be used for DNA diagnosis in cases of familial retinoblastoma.

Ref.: Friend S. H., et al.; PNAS 84, (24) 9059–63, 1987.

RET

The RET oncogene is frequently rearranged and recombined with another gene in papillary thyroid carcinomas. Germline mutations of the RET oncogene have been detected in a high percentage of patients with multiple endocrine neoplasms of the MEN 2A type and of patients with familial thyroid carcinoma (FMTC).

Ref.: Viglietto G et al.; oncogene 1995 Sep. 21, 11(6): 1207–10.

SCCA-1 (Squamous Cell Carcinoma Antigen-1)

The protein SCCA-1 was isolated from a metastatic cervical squamous cell carcinoma. SCCA-1 is used as marker for squamous epithelial carcinomas in particular of the cervix, of the throat and neck, of the lung and of the oesophagus, the amount of the antigen in the blood correlating with the progression.

Ref.: Schneider et al.; Proc. Natl. Acad. Sci. U.S.A. 92: 3147–3151, 1995.

P-, L- and E-Selectin

Selectins are transmembrane glycoproteins which are expressed on various cell types such as platelets (P-selectin), leukocytes (L-selectin) and endothelial cells (E- and P-selectin). The pattern of expression of the selectins and their ligands on cells provides information on the recirculation behaviour of the relevant cell.

Ref.: Springer, T. A. et al.; Cell 76: 301–314, 1994.

SF (Scatter Factor)

Synonym: hepatocyte growth factor (HGF)

SF is mainly expressed by mesenchymal cells, stroma and fibroblasts and is a potent angiogenesis and motility factor which, as a tumour cell autocrine factor, can enhance their invasiveness as well as tumorigenesis.

Ref.: Nakamura et al.; Nature 342: 440–443, 1989; Bellusci et al.; Oncogene 9: 1091–1099, 1994.

c-met SF Receptor

Synonym: met proto-oncogene

The c-met proto-oncogene plays an important part in the development of tumours.

Ref.: Park et al.; Proc. Natl. Acad. Sci. USA 84: 6379–6383, 1987.

STAT5 (Signal Transduction and Activator of Transcription 5)

STATs are a family of proteins which both perform a signal transduction function and are transcription activators.

Ref.: Darnell; PNAS 93: 6221–6224, 1996.

Surfactant Proteins

Synonyms: surfactant protein (SP)-A, -B, -C; -D

Surfactant protein A is, for example, expressed only by type II alveolar epithelial cells and Clara cells in lung tissue and SP-C is expressed exclusively by type II alveolar cells. There are several surfactant proteins (A1 and A2, B, C and D) whose expression (for example mRNA) has been described in metastatic, micrometastatic, pulmonary and extrapulmonary adenocarcinomas, non-small-cell lung carcinomas and breast carcinomas.

Ref.: Betz et al.; Cancer Res. 55: 4283–4286, 1995.

Telomerase

Telomerases define the ends of chromosomes.

Ref.: Morin G. B., et al.; Nature 353, 454–456, 1991. Blackburn E. H.; Nature 350, 569–573, 1991.

TGF-alpha (Transforming Growth Factor Alpha)

Synonyms: MDGF-2 (milk-derived growth factor 2); TGF-1; TCGF (transformed cell growth factor)

TGF-alpha is expressed by a large number of carcinomas and transformed (by viral or cellular oncogenes) cell lines. It may act as autocrine growth factor in ovarian carcinomas or as haematopoietic growth factor and may be involved in the vascularization of tumour tissue.

Ref.: Derynck; Advances in Cancer Research 58: 27–52, 1992.

TIMP (Tissue Inhibitors of Metalloproteinases)

The TIMPs belong to a family of inhibitors of the activity of metalloproteinases and thus counteract tissue disintegration and help determine the invasion and metastasis of carcinoma cells into the tissue.

Ref.: Apte et al.; Genomics 19: 86–90, 1994.

TNF-alpha (Tumour Necrosis Factor Alpha)

Synonyms: cachectin; monocyte/macrophage-derived TNF; cytotoxin (CTX); endogenous pyrogen; TNF-α

TNF-alpha exerts a direct cytotoxic and apoptotic effect on tumour cells.

Ref.: Wang et al.; Science 228: 149–154, 1985.

TNF-R1 p55

Synonyms: CD120a; cytotoxic TNF-R

TNF-R1 stands for human tumour necrosis factor receptor 1 and mainly mediates cytotoxicity and apoptosis.

Ref.: Loetscher H., et al.; Cell 61, 351–59, 1990.

TNF-R2 p75

Synonym: C120b; TNFBR

TNF-R2 mainly mediates T-cell activation.

Ref.: Beltinger C. P.; Genomics 35, 94–100, 1996.

Topoisomerase II

Synonyms: TOPO; TOP2A; topoisomerase alpha

DNA topoisomerases are ATP-dependent enzymes which control the topological status of DNA. Drug resistance may be found in tumours in which topoisomerase activity is reduced, such as, for example, by reduced expression. In addition, a mutation of the topoisomerase gene has been isolated from drug-resistant cell lines and has the effect that the enzyme is no longer inhibited by the chemotherapeutic agent.

Ref.: Hinds et al.; Cancer Research 51: 4729–4731, 1991.

Translocations and Rearrangements

B- and T-cell Receptor Rearrangements

There is rearrangement of the immunoglobulin (Ig) genes during B-cell differentiation and of the T-cell receptor (TCR) during T-cell maturation. If a multiplication of a T-cell clone is found in the blood of a patient, it can be identified against the polyclonal background of all the remaining T lymphocytes.

Ref.: Trainor et al.; Blood, 78, 192–196, 1991.

Lehman et al.; Am. J. Clin. Pathol. 103, 171–176, 1995.

Translocation (14;18)

This translocation is the commonest in human lymphomas. It is found in more than 80% of follicular lymphomas, in about 20% of diffuse large-cell lymphomas and in about 50% of adult undifferentiated lymphomas.

Ref.: Barker et al.; Blood, 83, 1079–1085, 1994.

Translocation (9;22)

Synonyms: Philadelphia chromosome, BCR/ABL

The Philadelphia chromosome is brought about by a reciprocal translocation between chromosomes 9 and 22 which is found in the tumour cells of about 90% of patients with chronic myeloid leukaemia (CML). A small incidence of this rearrangement is also found in acute lymphatic leukaemias. Only 3 different possible fusion transcripts result, and they can be used to detect a CML or minimal residual disease.
Ref.: Maurer et al.; The Lancet, 337, 1055–1058, 1991.

Translocations (2;13) and (1;13)

A specific cytogenetic abnormality found in 68% of alveolar rhabdomyosarcomas is translocation (2;13) in which the genes of transcription factors PAX3 (chromosome 2) and FKHR (chromosome 13) are involved.

14% of alveolar rhabdomyosarcomas have translocation (1;13) where the PAX7 gene on chromosome 1 is involved instead of the PAX3 gene on chromosome 2.
Ref.: Sreekantaiah et al.; American J. Pathol., 144: 1121–1134, 1194.

Translocation (x;18)

This translocation is found in 91% of all synovial sarcomas. The SSX gene of chromosome X and the SYT gene of chromosome 18 are involved, leading to a fusion transcript which presumably occupies a key position in the development of tumours.
Ref.: Clark et al.; Nature Genetics, 7, 502–508, 1994.

Translocation (12;16)

This translocation occurs in 77% of all myxoid liposarcomas and involves the genes of the transcription factor CHOP (chromosome 12) and the FUS gene (chromosome 16) whose function is still unknown.
Ref.: Rabbits et al.; Nature Genetics, 4, 175–180, 1993.

Translocation (11;22)

This translocation is found in 86% of all Ewing's sarcomas and results in the formation of a fusion transcript consisting of the EWS gene (chromosome 22) and the FLI gene (chromosome 11).
Ref.: West et al.; J. Clin. Oncol., 15, 583–588, 1997.

α- and β-tubulin

Tubulins are the monomer components of the microtubules of the cytoskeleton.
Ref.: J. Biol. Chem. 272:2534 (1997).

Tyrosinase

Tyrosinase is a key enzyme of melanin synthesis and is expressed only in melanocytes and melanoma cells. Detection of tyrosinase-expressing cells in the blood therefore indicates the presence of circulating melanoma cells in the blood.
Ref.: Giebel et al.; Genomics 9. 435–445, 1991.

UPA (Urokinase-Type Plasminogen Activator) and PAI-1 (Plasminogen Activator Inhibitor 1)

UPA is a proteolytic enzyme whose expression correlates with increased invasiveness, tumour-associated angiogenesis and metastasis. Its activity is regulated by an inhibitor (PAI-1). Investigations inter alia on primary breast carcinoma and gastric carcinoma have shown that high levels of UPA are associated with a poor prognosis. This is consistent with the lack of expression of PAI-1 in aggressive tumour cells. The balance between UPA and PAI-1 thus forms a prognostic parameter for the metastasis and angiogenesis ability of a tumour.
Ref.: Ito et al.; Virchows Arch. 427:487–497, 1996.

VEGF (Vascular Endothelial Growth Factor)

Synonyms: VPF; vascular permeability factor; vasculotropin; CD(glioma-derived)-VEGF VEGF may, as a consequence of alternative splicing of the mRNA, occur in four forms, namely VEGF121 and VEGF165, and VEGF189 and VEGF206. VEGF appears to play an important part in the control of blood vessel formation and permeability and moreover to be a main regulator of tumour angiogenesis.
Ref.: Leung et al.; Science 246: 1306–1309, 1989.

Tischer et al.; J. Biol. Chem. 266: 11947–11954, 1991.

VEGF-R1 (VEGF Receptor 1)

Synonyms: FMS-like tyrosine kinase-1; flt1 vascular endothelial growth factor/vascular permeability factor receptor; oncogene flt An increased expression of VEGF-R1 in carcinomas has frequently been described.
Ref.: Shibuya et al.; Oncogene 5: 519–524, 1990.

VEGF-R2 (VEGF Receptor 2)

Synonyms: KDR; tyrosine kinase growth factor receptor; FLK-1 receptor for vascular endothelial growth factor; FLK1; kinase insert domain receptor The up-regulation of VEGF mRNA in tumour cells and of the mRNA of its receptors in the tumour vasculature correlates with an increased aggressiveness of the tumour. VEGF-R2 is also transcribed in melanoma and ovarian tumour cells.
Ref.: Terman et al.; Oncogene 6: 1677–1683, 1991;

Boocock et al.; J. Natl. Cancer Inst. 87: 506–516, 1995.

VHL (Von Hippel-Lindau Syndrome)

The VHL gene product is a tumour suppressor protein which leads in the case of genetic mutations to renal carcinomas, haemangiomas of the cerebellum and retina, phaeochromocytomas and ependymomas. It has likewise been shown to be involved in the development of spontaneous tumours.
Ref.: Latif et al.; Science 260: 1317–1320, 1993.

Viral Oncogenes

Of particular importance for viral oncogenesis are hepatitis B and C viruses, possibly also SV40, in relation to hepatocellular carcinomas, the HTLV-1 virus in connection with T-cell lymphomas, the Epstein-Barr virus (EBV) in connection with Burkitt's lymphomas, nasopharyngeal carcinomas and Hodgkin's disease and human papillomaviruses of types 16 and 18 in connection with carcinomas in the urethrogenital region, in particular of the cervix.

In addition, herpesviruses of types 4 and 6 and the HI virus have been suggested to be connected with the development of tumours.

Ref.: Mueller M.; Environ. Health Perspect. 103 (1995) Suppl. 8, 259–261.

Hepatocellular Carcinomas
Ref.: De-Vita S. et al.; Blood 86 (1995) 1887–1892.
Koike K.; Intervirology 38 (1995) 134–142.
Casola S. et al.; Acta Genet. Med. Gemellol Roma 45 (1996) 221–225.
E Hara et al.; Dev. Genet. 18 (1996) 161–172.

Urethrogenital Carcinomas (Cervical Carcinomas, Vulval Carcinomas, Prostate Cancer, Anal Cancer, Bladder Cancer)
Ref.: Beyer-Finkler E. et al.; Intervirology 38 (1995) 173–180.
Moyet-Lalle C. et al.; Int. J. Cancer 64 (1995) 124–129.

Lymphomas (Non-Hodgkin Lymphomas, Burkitt's Lymphomas, T-Cell Lymphomas, B-Cell Lymphomas)
Ref.: Lee J. H. et al.; J. Korean Med. Sci. 10 (1995) 399–405;
Tomita Y. et al.; Leuk. Lymphoma 19 (1995) 129–134.
Wang C. Y. et al.; Mayo Clin. Proc. 70 (1995) 665–672;
Maroushek S. R. et al.; Microb. Pathog. 19 (1995) 317–333.

Lung Carcinomas
Ref.: Hogg J. C., Hegele R. G.; Semin Resp. Infect. 10 (1995) 244–253.

WT1
Wilms tumours are kidney tumours of children. It is very probably a tumour suppressor gene.
Ref.: Bonetta L., et al.; Cytogenet. Cell Genet. 51, 1989.
Gessler M., et al.; Genomics 12, 807–813, 1992.

The invention claimed is:

1. A method for determining an increased risk for or presence of a disseminated cancer cell or a micrometastasized cancer cell in a body fluid from a subject, comprising:
   (a) investigating, in a plurality of cells from a body fluid of a subject known to have or suspected of being at risk for having a disseminated cancer cell or a micrometastasized cancer cell, for at least one first nucleic acid selected from the group consisting of a cancer-specific mRNA and a cancer-associated mRNA, wherein the mRNA is essentially not expressed in a non-cancer cell in the body fluid;
   (b) isolating from the body fluid at least one cancer cell according to a method for removing cancer cells from non-cancer cells;
   (c) investigating at least one cancer cell isolated according to step (b) for at least one second nucleic acid selected from the group consisting of a cancer-specific nucleic acid and a cancer-associated nucleic acid; and
   (d) investigating at least one non-cancer cell from the body fluid for at least one second nucleic acid that is investigated in step (c) whereby a control is provided based on the body fluid,
   wherein said first and second nucleic acids are different, wherein presence of said first nucleic acid in the plurality of cells and an increased or decreased presence of the second nucleic acid in the cancer cell relative to the presence or absence of said second nucleic acid in the non-cancer cell from the body fluid indicate an increased risk for having a disseminated cancer cell or a micrometastasized cancer cell.

2. The method of claim 1 wherein the mRNA that is essentially not expressed in a non-cancer cell in the body fluid comprises all or a portion of a transcript of a gene selected from the group consisting of a CEA gene, a CK20 gene, a MUC1 gene, a tyrosinase gene and a MAGE3 gene.

3. The method of claim 1 wherein the cancer cell is removed from the body fluid by a method selected from the group consisting of microfiltration, density gradient centrifugation and antigen-specific immunoadsorption.

4. The method of claim 1 wherein the mRNA that is essentially not expressed in a non-cancer cell in the body fluid encodes an organotypical gene, and wherein the presence of at least one of said mRNA encoding an organotypical gene indicates the type of malignant disease from which the cancer cell is derived.

5. The method according to claim 1 wherein steps (a)–(d) are performed before and after administering a candidate anticancer therapy to a subject known to have or suspected of being at risk for having a disseminated cancer cell or a micrometastasized cancer cell.

6. The method of claim 1 wherein the first nucleic acid is a first cancer-specific mRNA and the second nucleic acid is a second cancer-specific nucleic acid.

7. The method of claim 1 wherein the first nucleic acid is a first cancer-specific mRNA and the second nucleic acid is a cancer-associated nucleic acid.

8. The method of claim 6 or 7 wherein the second nucleic acid is selected from the group consisting of DNA and RNA.

9. The method of claim 8 wherein the RNA comprises mRNA.

10. The method of claim 9 wherein the mRNA encodes a gene product selected from the group consisting of bFGF, bFGF-R, VEGF, VEGF-R1, VEGF-R2, MMP2 and TIMP3.

11. The method of claim 8 wherein the DNA that is detected comprises genomic DNA selected from the group consisting of genomic DNA comprising a genomic mutation, genomic DNA comprising a gene that has undergone amplification, genomic DNA comprising a gene that has undergone loss of heterozygosity, genomic DNA comprising a translocated gene and genomic DNA comprising a gene polymorphism.

12. The method of claim 11 wherein the genomic DNA comprises all or a portion of a gene selected from the group consisting of a p53 gene, an erb-B2 gene, a c-myc gene, a K-ras gene, an RB gene, an APC gene and a DCC gene.

13. The method of claim 8 wherein the DNA is genomic DNA that comprises all or a portion of an oncogene.

14. The method of claim 8 wherein the DNA is genomic DNA that comprises all or a portion of a tumor suppressor gene.

15. The method of claim 7 wherein the cancer-associated nucleic acid comprises a coding portion of a gene selected from the group consisting of a tissue-specific gene, a metastatis-associated gene, a steroid hormone receptor gene, a drug resistance gene, an immunomodulation gene, a cell proliferation gene and an apoptosis gene, or a complementary nucleic acid thereto.

16. The method of claim 15 wherein the metastasis-associated gene encodes a gene product selected from the group consisting of an angiogenesis factor, a motility factor, a growth factor, a matrix degradation factor and an adhesion factor.

17. The method of claim 16 wherein the matrix degradation factor is selected from the group consisting of a proteinase and a proteinase inhibitor.

18. The method of claim 16 wherein the adhesion factor is an adherin.

19. The method of claim 1 wherein said step of investigating, in a plurality of cells from a body fluid of a subject, for the mRNA that is essentially not expressed in a non-cancer cell in the body fluid takes place without previous removal of cancer cells from the plurality of cells.

20. The method of claim 19 wherein the body fluid is blood and the plurality of cells is the buffy coat or a mononuclear cell fraction derived from blood.

21. The method of claim 1 wherein the disseminated or micrometastasized cancer cell originates from a primary tumor.

* * * * *